(12) United States Patent
Kalish

(10) Patent No.: US 9,420,867 B2
(45) Date of Patent: Aug. 23, 2016

(54) HAND CLEANING DEVICE

(71) Applicant: Jonathan Reed Kalish, Tupelo, MS (US)

(72) Inventor: Jonathan Reed Kalish, Tupelo, MS (US)

( * ) Notice: Subject to any disclaimer, the term of this patent is extended or adjusted under 35 U.S.C. 154(b) by 203 days.

(21) Appl. No.: 14/196,565

(22) Filed: Mar. 4, 2014

(65) Prior Publication Data

US 2015/0128365 A1     May 14, 2015

Related U.S. Application Data

(60) Provisional application No. 61/901,936, filed on Nov. 8, 2013.

(51) Int. Cl.

| A47K 7/03 | (2006.01) |
|---|---|
| A47K 7/04 | (2006.01) |
| A61L 2/26 | (2006.01) |
| A45D 29/17 | (2006.01) |
| A45D 29/00 | (2006.01) |
| A45D 34/00 | (2006.01) |
| A47K 5/12 | (2006.01) |

(52) U.S. Cl.
CPC ............... *A45D 29/17* (2013.01); *A45D 29/00* (2013.01); *A45D 34/00* (2013.01); *A47K 7/03* (2013.01); *A47K 7/043* (2013.01); *A61L 2/26* (2013.01); *A47K 5/1201* (2013.01); *A61L 2202/16* (2013.01)

(58) Field of Classification Search
CPC ...... A47K 5/1201; A47K 7/03; A47K 7/043; A45D 29/007; A46B 2200/1013; A61B 19/36; A61L 2202/16

USPC .................. 401/6, 7, 10, 11, 152, 154, 156, 401/183–186, 206, 264, 265

See application file for complete search history.

(56) References Cited

U.S. PATENT DOCUMENTS

| 1,437,177 | A | 11/1922 | Hartman |
|---|---|---|---|
| 2,777,141 | A | 1/1957 | Nye |
| 2,841,811 | A | 7/1958 | Carrol |
| 3,014,579 | A | 12/1961 | Lathrop |
| 3,387,313 | A | 6/1968 | Smith et al. |
| 3,467,978 | A | 9/1969 | Golden |
| 4,181,446 | A | 1/1980 | Kaufman |
| D271,817 | S | 12/1983 | Collin |
| 4,420,853 | A | 12/1983 | Gilman et al. |

(Continued)

FOREIGN PATENT DOCUMENTS

JP     2009005893     1/2009

OTHER PUBLICATIONS

Unilever, "Active Clean Dual Sided Shower Tool," published 2013, 1 page.

(Continued)

*Primary Examiner* — Jennifer C Chiang
*Assistant Examiner* — Joshua Wiljanen
(74) *Attorney, Agent, or Firm* — Banner & Witcoff, Ltd.

(57) ABSTRACT

A device for reducing a level of infectious agents present on one or more hands of a user. This device may reduce the level of infectious agents present on one or more fingers and/or thumbs of a user, specifically reducing a level of infectious agents present on the distal aspect of the digit; including, but not limited to an underside of a nail plate, and an area of hyponychium skin between a free margin of the nail plate and an onychodermal band of a digit, such as for example, a finger, thumb, or toe.

19 Claims, 10 Drawing Sheets

(56) References Cited

U.S. PATENT DOCUMENTS

| | | |
|---|---|---|
| 4,479,277 A | 10/1984 | Gilman et al. |
| 4,480,351 A | 11/1984 | Koffler |
| D290,533 S | 6/1987 | Kadaja |
| 4,730,949 A | 3/1988 | Wilson |
| 4,757,571 A | 7/1988 | Young |
| 4,866,806 A | 9/1989 | Bedford |
| 4,886,078 A | 12/1989 | Shiffman |
| 4,939,529 A | 7/1990 | Kanayama et al. |
| 5,312,197 A | 5/1994 | Abramson |
| 5,355,545 A | 10/1994 | Hoagland |
| 5,596,785 A | 1/1997 | Park |
| 5,836,034 A | 11/1998 | Galvan Garza |
| 6,016,812 A | 1/2000 | Guynn |
| 6,102,048 A | 8/2000 | Baker |
| 6,174,577 B1 * | 1/2001 | Vitorino ............... D06F 58/203 428/36.5 |
| 6,289,547 B1 | 9/2001 | Narula et al. |
| 6,370,724 B1 | 4/2002 | Holmes et al. |
| 6,813,798 B2 | 11/2004 | Moga |
| 6,821,043 B2 | 11/2004 | Teh |
| D505,267 S | 5/2005 | Woods |
| 7,260,863 B2 | 8/2007 | Kaufman et al. |
| D554,816 S | 11/2007 | Lee et al. |
| D559,460 S | 1/2008 | Garland et al. |
| 7,597,122 B1 | 10/2009 | Smith |
| D623,356 S | 9/2010 | Lee et al. |
| D623,802 S | 9/2010 | Lee et al. |
| 8,230,544 B2 | 7/2012 | Leshko |
| 8,393,337 B2 | 3/2013 | Kalish et al. |
| 8,408,217 B2 | 4/2013 | Kalish et al. |
| 8,893,727 B2 | 11/2014 | Kalish et al. |
| 2003/0081980 A1 | 5/2003 | Moga |
| 2004/0101347 A1 | 5/2004 | Beard |
| 2006/0186135 A1 | 8/2006 | Rose et al. |
| 2006/0196519 A1 | 9/2006 | Strickland et al. |
| 2013/0104921 A1 | 5/2013 | Shammami |

OTHER PUBLICATIONS

Laser, "Mechanics Nail Brush," published 2010, 1 page.

* cited by examiner

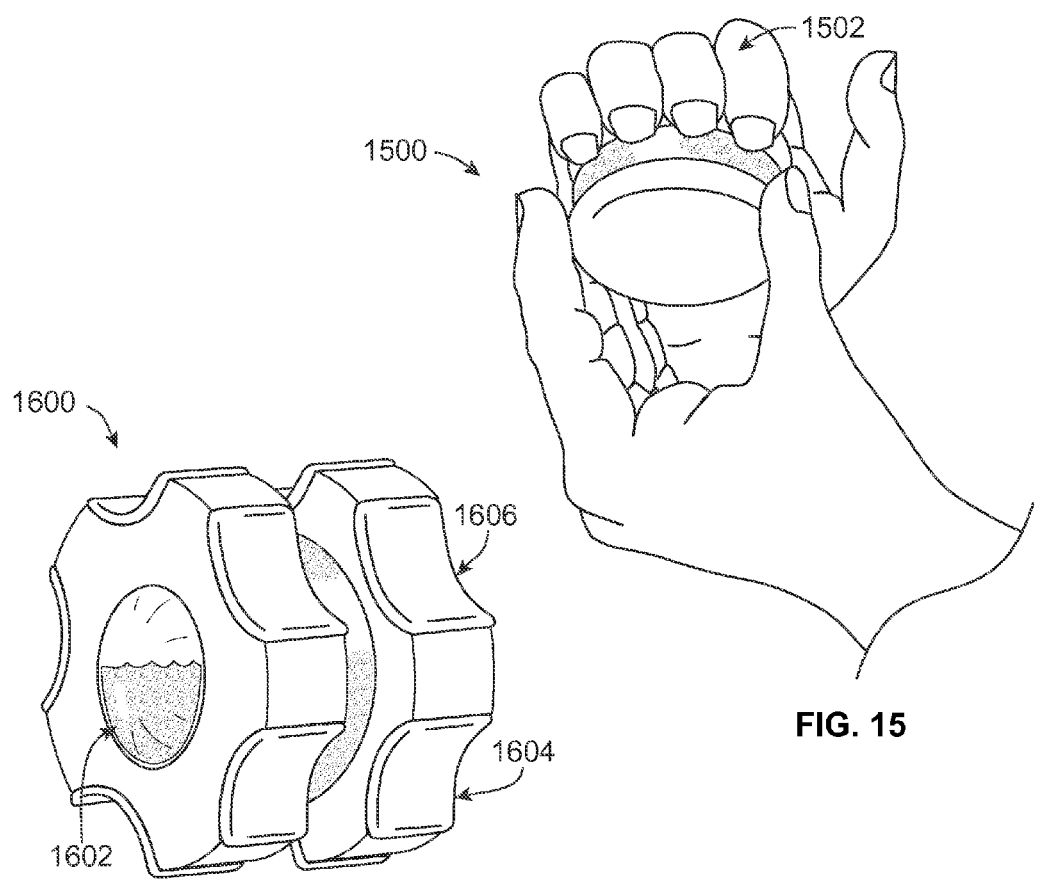
FIG. 15
FIG. 16
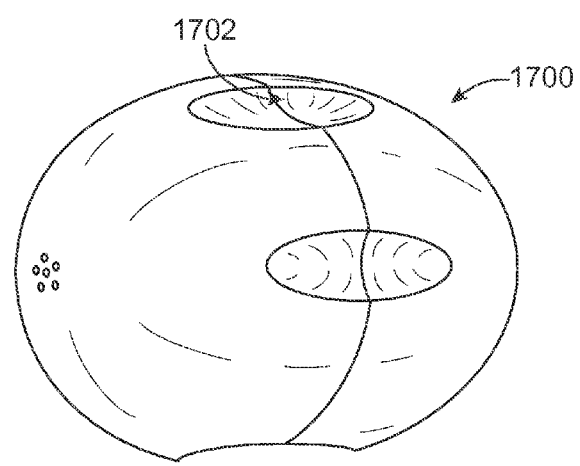
FIG. 17

HAND CLEANING DEVICE

BACKGROUND

Inherently, a person's hands may interact with one or more environments, objects, animals, or other people throughout the course of daily life. Accordingly, a person's hands may come into contact with, and present one or more surfaces that may allow for retention of, and subsequent transmission of, various forms of infectious agents. Infectious agents are otherwise referred to as pathogens, or "germs," and may include, among others, viruses, bacteria, fungi, protozoa, and parasites. Furthermore, the presence of one or more infectious agents on a person's hands may lead to said person contracting, or transmitting, one or more communicable (transmissible) diseases. As such, it is beneficial for people to wash their hands regularly.

Various cleaning agents (such as, among others, antibacterial hand washes, surfactants (soaps), and sanitizers, and the like), in addition to various tools (such as, among others, scrubbing brushes, nail picks, and the like), are known in the art for aiding in reducing a level of infectious agents present on a person's hands. However, in spite of the availability of various materials and tools, it is known that various communicable diseases are still transmitted due to improper hand cleaning technique, and/or a frequency of hand cleaning that is inadequate. This issue of transmission of one or more communicable diseases as a result of contact, and subsequent retention of one or more infectious agents on a person's hand is of particular importance for diverse environments, ranging from restaurants to laboratories and hospitals. In this specific example, a healthcare worker may contaminate his/her hands through contact with one or more patients infected with one or more communicable diseases. In some instances, the infectious agents (microorganisms) contaminating the healthcare worker's hands may survive on skin for the length of time ranging from minutes to hours, and may spread to their clothing if they are not adequately removed. In this example, if the healthcare worker does not thoroughly clean his/her hands after contact with the one or more infected patients, and before contact with one or more healthy persons, transmission of the one or more communicable diseases may result. Furthermore, and as identified in a World Health Organization study (*WHO Guidelines on Hand Hygiene in Health Care: a Summary,* 2009), the incidence of contraction of one or more infections due primarily to transmission within a clinical environment ranges from 4.5% to 19% and above in various countries for which information was presented. Additionally, transmission by contaminated healthcare workers hands was identified as one of the most common methods. This issue is not restricted to just healthcare workers. Indeed, recent outbreaks of the influenza virus have demonstrated. The quick and devastating effects of human to human transmission, and ineffective hand-washing continues to be one of the primary causes of this transmission.

Even if individuals make appropriate efforts to clean their hands frequently, they may not employ the appropriate technique, and therefore not reduce the level of infectious agents present on one or more hands (or portion thereof) enough to prevent the transmission of communicable diseases. In particular, it may be found that a relatively high concentration of infectious agents may be retained in proximity to the nails of a hand of a user after a cleaning process when compared to the surface area of skin of a hand as a whole. Specifically, a high concentration of infectious agents may be present on an underside of a nail plate, and on an area of skin proximate to the nail plate, (i.e., the hyponychium skin between a free margin of the nail plate and an onychodermal band of a finger or any digit). As such, the need exists for a device, and for associated methods, for improving cleaning appendages, including hands and feet.

BRIEF SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects described herein relate to a device for cleaning appendages, such as for example, human hands. In certain embodiments, a device may reduce the level of infectious agents present on one or more fingers and/or thumbs of a user, specifically reducing a level of infectious agents present on the distal aspect of the digit; including, but not limited to an underside of a nail plate, and an area of hyponychium skin between a free margin of the nail plate and an onychodermal band of a digit, such as for example, a finger, thumb, or toe. In various implementations, it may be a unitary device.

An example device may have a body composed of at least one compressible material, which may be configured to retain a cleaning agent within at least a portion of the body. The body may be configurable to transition from a first compressed state to an expanded second state upon being exposed to at least one of: an increase of an atmospheric pressure force above an atmospheric pressure threshold and a decrease in a compressive force below a compressive force threshold. The device, when in one or more states, may include hand-placement structures comprising an outer surface configured to receive a palm. Hand placement structures may, with respect to a first horizontal axis, oppose each other.

One or more example devices may include at least one digit cleaning region. A region may be positioned, with respect to the horizontal axis, between a first hand-placement structure's outer surface and a second hand-placement structure's outer surface. The region may be configured to receive at least a portion of a plurality of digits of each of the first and the second hand of the user and upon use of the device to reduce a level of infectious agents present on the distal aspect of at least one digit, including but not limited to an underside of a nail plate of each of the plurality of digits as well as an area of hyponychium skin between a free margin of the nail plate and an onychodermal band of each of the plurality of digits.

Certain devices may be configured to expand, such as for example when the atmospheric pressure threshold is at about or above the standard atmospheric pressure of 101.325 kPa. Transitioning of the device and/or the release of one or more cleaning agents from the device may be configured to occur when the device is exposed to at least one of: an atmospheric pressure force meeting an atmospheric pressure threshold, a compressive force meeting a compressive force threshold, and a twisting or rotational force upon a portion of the body.

In certain embodiments, at least a portion of the body is degradable and the device is configured to decompose during use of the device. Decomposition may be at a rate coincident with an intended use time frame of the device. A device may include at least a first material configured to degrade at a first rate and a second material configured to degrade at the second rate. In further embodiments, the device is configured such that during use, at least one of: a force of the user's digits and a rotational force of the device along an axis of rotation is configured to expose a cleaning agent held within the device to be extruded onto at least a portion of the user's digits on or in the device. In other embodiments, at least one of the force of the user's digits and the rotational force of the device is configured to result in the atraumatic cleaning of the distal aspect of the digit including the underside of a nail plate of the plurality of digits within the cavities as well as an area of hyponychium skin between a free margin of the nail plate and an onychodermal band of each of the plurality of digits.

The device may include a plurality of openings aligned with a plurality of cavities, and configured to receive one or more fingers and/or thumbs of the user. The hand cleaning device further may include a barrier structure between adjacent cavities to reduce transmission of an infectious agent between cavities. Furthermore, the hand cleaning device includes an exterior outlet and an interior outlet for release of a cleaning agent onto the hand and/or portion thereof (e.g., fingers) of the user. In another embodiment, the hand cleaning device may have a lip structure within a cavity, for increasing a surface area of hyponychium skin that is exposed to a cleaning agent.

In yet another embodiment, the hand cleaning device may have a cleaning agent reservoir for holding a cleaning agent to be released onto one or more hands of the user. The hand cleaning device may have a release mechanism within the device enclosure structure for releasing the cleaning agent onto one or more hands of the user. The hand cleaning device may, in one embodiment, comprise one or more of a porous material, an abrasive material for scrubbing skin of the user, or a degradable material. In yet another embodiment, the hand cleaning device may comprise a cylindrical shaped structure. In another embodiment, the hand cleaning device may expand from a compressed state with a substantially cylindrical shape into an uncompressed state with a substantially spherical shape.

In yet another aspect, this disclosure relates to a device for reducing a level of an infectious agent on a hand of the user and for reducing transmission of the infectious agent between two fingers, two thumbs, or a finger and/or any digit of a user. The device has a divider structure separating a first hand-placement structure and a second hand-placement structure, for separating the fingers and/or any digit of a first hand of the user from the fingers and/or thumb of a second hand of a user. The device further has an inlet for receiving a hand cleaning material and an outlet for releasing that hand cleaning material onto one or more hands of the user.

This Summary is provided to introduce a selection of concepts in a simplified form that are further described below in the Detailed Description. The Summary is not intended to identify key features or essential features of the claimed subject matter, nor is it intended to be used to limit the scope of the claimed subject matter.

BRIEF DESCRIPTION OF THE DRAWINGS

Aspects of the invention are illustrated by way of example and not limited in the accompanying figures in which like reference numerals indicate similar elements and in which:

FIG. 15 depicts an implementation of a hand cleaning device in operation, in accordance with one illustrative embodiment;

FIG. 16 schematically depicts a hand cleaning device in accordance with one illustrative configuration;

FIG. 17 depicts a hand cleaning device in accordance with another illustrative embodiment.

Figure 1:
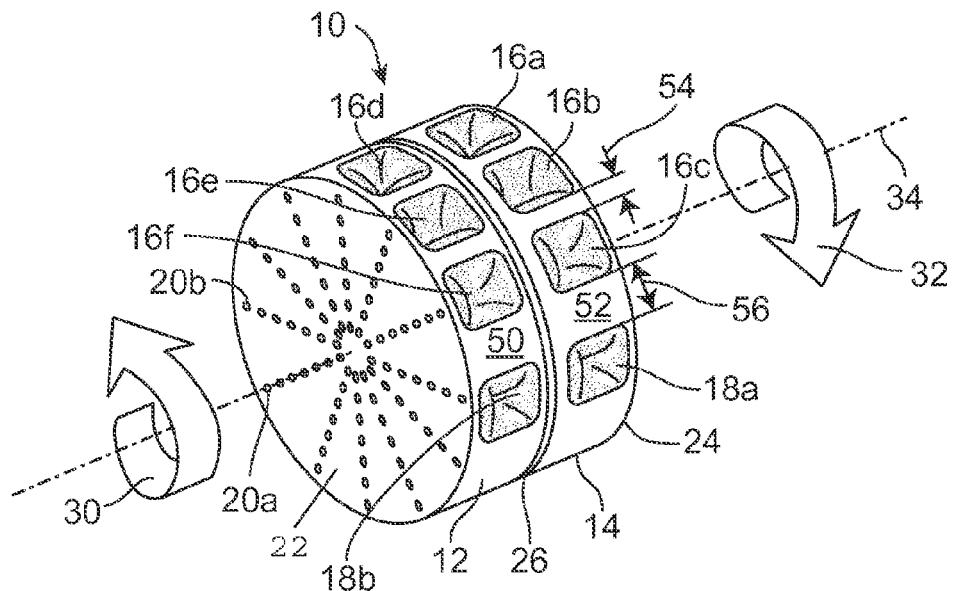
FIG. 1 depicts one example hand cleaning device in accordance with one illustrative embodiment.

The reader is advised that although certain implementations of cleaning devices, such as those shown in FIGS. 1-17 may contain the dimensions or scale of those depicted or described herein, the drawings are not drawn to scale with respect to each and every embodiment within the scope of this disclosure. Therefore, the scope of this disclosure, inclusive of the claims, is not limited to the scale shown in the drawings, unless otherwise explicitly indicated.

Aspects of this disclosure relate to a device for reducing a level of infectious agents present on one or more appendages of a user. Although many descriptive embodiments are described in reference to a human hand, those skilled in the art with the benefit of this disclosure will readily appreciate that these embodiments are not limited to human hands, but rather encompass feet, and other human and non-human appendages. For example, the inventors have envisioned veterinary uses of the disclosed embodiments. Therefore, the reader is advised that the embodiments disclosed herein are not limited to human hands, unless expressly indicated. In certain embodiments, a device may reduce the quantity and/or the infectious capabilities (e.g., through attenuation) of infectious agents present on one or more digits of a user, specifically reducing a level of infectious agents present on an underside of a nail plate, and an area of hyponychium skin between a free margin of the nail plate and an onychodermal band of a digit, such as a finger, thumb and/or toe. In this regard, many embodiments described herein are discussed in reference to human fingers. Those skilled in the art with the benefit of this disclosure, however, will readily appreciate that these embodiments are not limited to fingers, but may encompass at least one thumb and/or toe, alone or in combination with each other.

In the following description of various example structures, reference is made to the accompanying drawings, which form a part hereof, and in which are shown by way of illustration various example nail cleaning device structures in accordance with the invention. Additionally, it is to be understood that other specific arrangements of parts and structures may be utilized, and structural and functional modifications may be made without departing from the scope of the present invention. Also, while the terms "top," "bottom," "front," "back," "rear," "side," "underside," "overhead," and the like may be used in this specification to describe various example features and elements of the invention, these terms are used herein as a matter of convenience, e.g., based on the example orientations shown in the figures and/or the orientations in typical use. Nothing in this specification should be construed as requiring a specific three dimensional or spatial orientation of structures in order to fall within the scope of this disclosure.

Additionally, while various embodiments are described in this disclosure and the accompanying figures, it will readily apparent to one of ordinary skill that other embodiments may be envisioned and/or various combinations of the elements depicted in the figures may be realized without departing from the scope of this disclosure. Furthermore, as noted above, the figures are not required to be drawn to scale, and where one or more implementations of cleaning devices for cleaning one or more hands of a user are presented, it will be readily apparent to those of skill that the embodiments described herein may be configured for use by users with differing hand sizes, and correspondingly, differing finger and thumb sizes. Accordingly, the one or more embodiments of a hand cleaning device, or combinations of the embodiments described herein, may be configured to accommodate, among others, an average hand size of children aged between 4 years and 17 years old, an average hand size of a grown adult, or an average hand size of a range of people aged from 4 years old to adulthood, and the like. Yet, in other embodiments, devices may be sized to fit a human of any age. Specific implementations may have discrete size groups that may be configured for use by certain age groups. In yet other embodiments, one or more devices may be shaped and/or sized for use with non-human beings. Such implementations may be beneficial for veterinary use.

FIG. 1 depicts one embodiment of a hand cleaning device 10. In one implementation, hand cleaning device may be primarily configured as a unitary device for surrounding a part of every digit of both hands of a user simultaneously. In this exemplary embodiment, hand cleaning device 10 has a substantially cylindrical shape. The cylinder may, such as in the illustrated embodiment, resemble a puck-like structure. Other shapes, however, may be utilized. For example, certain implementations may be elliptical and/or oblong. In this regard, a user's hand often may not be able to conform to a circular structure, such as when gripping said structure. Thus, certain embodiments, may use on or more irregular shapes that allow a user to better conform the placement of one or more digits, palm, and/or entire hand to one or more structures. Looking to FIG. 1, the device 10 may include, among others, a first hand-placement structure 12, and a second hand-placement structure 14. In one embodiment, the hand-placement structure 12 and the second hand-placement structure 14 may be mirror-images of each other. Device 10 is further illustrated to include an optional divider structure 26. The divider structure may be a non-permeable barrier, yet in other embodiments, distance alone, without a physical structure configured specifically to serve as a barrier, may serve as a barrier. As provided throughout this disclosure, a distance between two locations of the device may be beyond a distance threshold that reduces and/or prevents the risks of cross-contamination. In certain embodiments, a porous material may even be utilized between two areas (either as a physical barrier specifically designed to be positioned between two locations, or alternatively, as part of the physical structure of the device that is not specifically provided only as a barrier to prevent or reduce cross-contamination. It is well known in the art that different porous structures have different porosity. Thus, a porous structure may be used in which its porosity characteristics reduce and/or prevent cross-contamination due to the fact that the time it takes for contaminates to travel through pores exceeds the estimated use time of the device.

In certain embodiments disclosed below, a separation length may correspond to a thickness of a permeable (or sponge-like) material, wherein migration of one or more infectious agents through said thickness of said permeable material progresses at a rate that is greater than an average time to clean one or more hands of a user using cleaning device 10, and such that transmission of an infectious agent between two digits, two thumbs, or a finger and a thumb or any two digits is reduced or prevented during usage. Expected forces acting on the porous material(s) during use of the device may also be considered when determining the ability to serve as structures/distances that reduce or prevent cross-contamination. In other embodiments, a user pressing their digits down onto the material of device 10 may compress a compressible material, such that pores of the compressible materials are shut or otherwise substantially blocked by the force (and/or rotational force of the device) and thus reduces and/or prevents cross-contamination, such as between different hands and/or different digits.

Looking again to FIG. 1, a first hand-placement structure 12 and a second hand-placement structure 14 are shown with a plurality of openings (16a-16f and 18a-18b). As shown in the example of FIG. 1, each opening may be configured to receive a digit, such as for example, a finger or thumb, a plurality of exterior outlets (20a-20b). These openings which may generally be considered within a digit cleaning region. The device may be configured to rotate, such as for example, along an axis of rotation 34. Axis 34 is shown for illustrative purposes only and those skilled in the art will appreciate that one or more other axis of rotation may be utilized. In this regard, axis 34 may be implemented through one or more structures that permit two or more components to rotate in relation to one another, such as a mechanical structure. Examples of exemplary structures are provided herein. Yet in other embodiments, one or more components of device 10 may be configured to permit flexing and/or stretching of one or more components, such as for example, the first and second hand placement structures, among others, without a specific predetermined axis of rotation. As depicted in the figures, including for example FIG. 2, hand cleaning device 10 may be configured to clean one or more appendages, such as for example, a first hand 36 and/or a second hand 38 of the user. In particular, openings 18a and 18*b* may be configured to receive a first thumb 40*a* and a second thumb 40*b*, respectively, and openings 16*a*-16*f* configured to receive fingers 42*a*-42*f* respectively. In one example, openings 16*a*-16*f* and 42*a*-42*f* are configured to surround part of each digit of each hand of a user simultaneously.

It will be readily apparent to those of skill that hand cleaning device 10 may be embodied with different configurations of openings. For example, first hand-placement structure 12 may comprise a number of openings (16*d*-16*f* and 18*b*) on a surface 50 (wherein the surface 50 corresponds, in one implementation, to a perimeter of a cylindrical shape of hand-placement structure 12, and wherein the surface 50 may alternatively be referred to as a face 50 of hand cleaning device 10) that is less than, equal to, or greater than, a combined number of fingers and thumb of a first hand 36 of the user. Similarly, second and-placement structure 14 may comprise a number of openings (16*a*-16*c* and 18*a*) that is less than, equal to, or greater than, a combined number of fingers and thumb of a second hand 38 of a user. In certain embodiments, face 50 may be a veneer or structure that merely provides guidance to the user for ideal or preferred spacing of one or more digits. In this regard, there is no requirement in certain embodiments that one or more openings are defined by a connection between the face 50 and the respective opening. In this regard, the device 10 may be "open faced" such that the device 10 is devoid of any structures at about the face 50 that guide the user's digits into one or more predetermined locations. Other portions of a hand placement structure may include guides that assist the user is positioning their hand. For example, other surfaces may comprise one or more indentations or ridges that suggest proper placement of the user's hand and/or a portion thereof. As discussed throughout this disclosure, certain areas may comprise one or more deformable materials configured to deform upon placement of the user's hand or portion thereof.

In one implementation, an opening may be configured to receive any digit of a user, such as, for example opening 18*a* may be configured to receive thumb 40*a* of a user. In another implementation, an opening may be configured to receive a finger of a user, for example, opening 16*a* may be configured to receive finger 42*a* of a user. In yet another implementation, an opening may be configured to receive any one of a finger, thumb, or any digit of a user, or multiple digits. Accordingly, the openings of device 10, such as openings 16*a*-16*f* and 18*a*-18*b* may be configured with a size that is equal to or greater than a width of the largest digit, e.g., finger, thumb, or toe of a user. In another implementation, openings 16*a*-16*f* and 18*a*-18*b* may be configured with a size that is less than a width of one or more digits of a user, and wherein the construction of device 10 is such that one or more openings 16*a*-16*f* and 18*a*-18*b* expand upon insertion of a finger or any digit of the user. Accordingly, hand cleaning device 10 may comprise one or more deformable materials, and one or more openings 16*a*-16*f* and 18*a*-18*b* may deform upon insertion of a finger or any digit of the user. As discussed above, face 50 may merely define specific locations for insertion of digits; therefore, openings may not be present or partially present, until a user presses their finger against the location set by the face. Thus, in accordance with certain embodiments, the location of at least a portion of a digit cleaning region may be dependent of the configuration and/or use of the device. In further embodiments, face 50 may be partially or entirely absent. In one embodiment, location of openings will depend on the user's interaction with the device.

Returning to FIG. 1, in one implementation, cleaning device 10 may be constructed from one or more materials including, among others, one or more polymers, fiber-reinforced polymers, metals, alloys, ceramics, plant material (for example, wood, or cellulose wood fibers, and the like), natural sponges, synthetic materials that exhibit one or more properties of high compressibility, high absorbency, or a texture with abrasive qualities suitable for scrubbing skin (synthetic sponges), and/or combinations thereof. For example, in one implementation, the first hand-placement structure 12 and second hand-placement structure 14 may be constructed from a polymer (for example, acrylonitrile butadiene styrene (ABS)), and the divider structure 26 may be constructed from a synthetic sponge material. Additionally, the openings (16*a*-16*f* and 18*a*-18*b*) may be aligned with one or more cavities of a digit cleaning region, wherein said one or more cavities may be constructed from a same, or a different synthetic sponge material. In another implementation, hand cleaning device 10 may be entirely constructed from a single material, for example, a synthetic sponge material. In various embodiments, a digit cleaning region may encompass a portion of the hand-placement structures, including for example, an inner surface. In yet other embodiments, which are described herein, there may not be a distinct division between a hand-placement region and a digit cleaning region. In some embodiments, the digit cleaning region may be positioned between the first hand-placement structure's outer surface and the second hand-placement structure's outer surface. In certain embodiments, a digit cleaning region may be any area that, during intended or normal operation of the device, is configured or intended to clean at least the distal aspect of two or more digits of a user.

In one implementation, cleaning device 10 may have a separation length 54 between two openings, such as, for example, opening 16*b* and opening 16*c*. Separation length 54 may, in one implementation, be equal to an average separation between two digits of a user. For example, separation length 54 may be equal to an average separation between digits 42*b* and 42*c*, which, in turn, may correspond to an average hand size of a fully grown adult. In other implementations, separation length 54 may equal an average separation between two digits of a user, which may a specific age group or population dynamic. Similarly, cleaning device 10 may have a separation length 56 between two openings, such as, for example, 16*c* and 18*a*. Separation length 56 may, in one implementation, be equal to an average separation between a finger and a thumb of a user, and the like. In yet another implementation, separation length 54 and/or separation length 56 may correspond to a thickness of a permeable (or sponge-like) material, wherein migration of one or more infectious agents through said thickness of said permeable material progresses at a rate that is greater than an average time to clean one or more hands of a user using cleaning device 10, and such that transmission of an infectious agent between two digits, two thumbs, or a finger and a thumb or any two digits is reduced or prevented during usage. In another embodiment, separation length 54 and/or separation length 56 may correspond to a thickness of an impermeable material, wherein transmission of one or more infectious agents through said impermeable material between, two digits, two thumbs, or any digit is substantially eliminated. In one embodiment, the separation length between two openings may be defined by a force exerted by the user using the device. In this regard, a user pressing their digits down onto the material of device 10 may compress a compressible material, such that pores of the compressible materials are shut or otherwise substantially blocked by the force (and/or rotational force of the device) and thus, each digit does not contaminate an adjacent digit during use.

Figure 2:
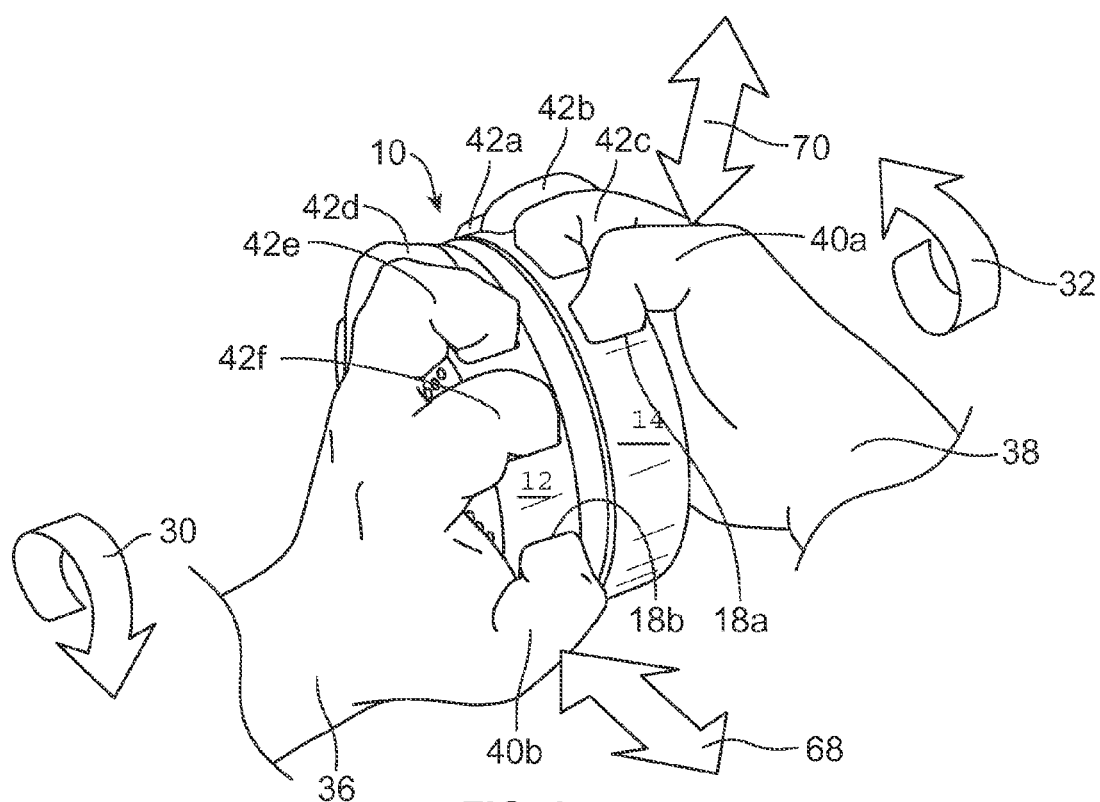
FIG. 2 depicts an example operation of a hand cleaning device from FIG. 1 in accordance with one illustrative embodiment.
Figure 10:
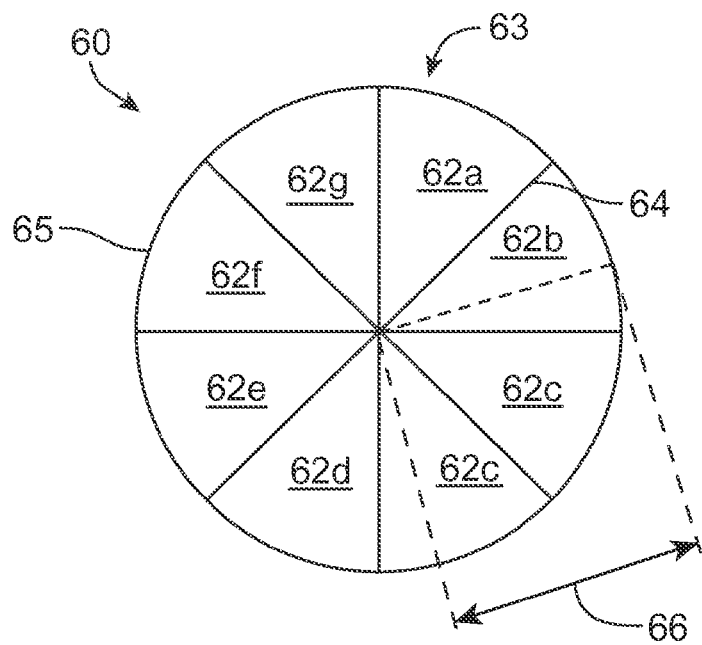
FIG. 10 depicts a schematic cross-sectional view of an example hand cleaning device in accordance with yet another embodiment.

FIG. 2 depicts an example operation of a hand cleaning device, such as device 10 from FIG. 1, in accordance with one implementation. In particular, FIG. 2 depicts a first hand 36 and a second hand 38 positioned on a first hand-placement structure 12, and a second hand-placement structure 14, respectively. As depicted FIG. 2, one or more openings 16a-16f and 18a-18b may be aligned with one or more cavities, for receiving one or more respective fingers (42a-42f) and/or thumbs (40a-40b) of a user. In one embodiment, one or more cavities for receiving a finger and/or any digit of a user are depicted in FIG. 10, which is discussed in more detail later in this disclosure. One or more cavities may be configured with a depth dimension of at least an average length of a distal digit or distal aspect of a user's one or more fingers and/or thumbs. In this regard, reference to the distal digit or a "distal aspect" of a finger, thumb, toes or any other digit refers to the portion of that digit. Thus, tissues and other anatomical structures (e.g. nail band, etc.) of the distal digit should be considered. For example, references to the length of the distal aspect should be interpreted as encompassing the tissue positioned around the terminus of the distal digit. Further, reference to structures or areas of a device, such as cavities, that are configured to "envelop" or "surround" the distal aspect of a digit refer to structures configured to receive the distal aspect/distal portion of the digit and further comprising components, such as walls or formations, configured to or capable of being manipulated to form a perimeter around the distal aspect/distal portion of the digit such that it is configured to permit (via one or more mechanisms), the atraumatic cleaning of the distal aspect of that digit during use of the device.

As best shown in FIGS. 1, outlets 20a and 20b represent a plurality of outlets through which one or more cleaning agents/cleaning materials may be released from within hand cleaning device 10. However, other embodiments of hand cleaning device 10 may be envisioned, wherein first hand-placement surface 22 comprises a single outlet (e.g., 20a or 20b), or alternatively, first hand-placement surface 22 comprises a different configuration/pattern of outlets to those depicted in FIG. 1. In one implementation, a cleaning agent may comprise a hand sanitizer, a disinfectant solution, or a soap, and/or any material known in the art for use in killing and/or removing infectious agents from skin. Additionally, while this disclosure may refer to a hand cleaning agent, those of ordinary skill in the art will understand that's such a hand cleaning agent may be a cleaning agent designed for use on feet of the user, or on another area of skin, without departing from the descriptions of this disclosure. In certain embodiments, two or more components may be combined to form the cleaning agent. In certain embodiments, at least one component may be water to serve as a diluent. In yet other embodiments, water alone may serve as the cleaning agent. In one embodiment, cleaning agent may be encapsulated within an enclosure structure of hand cleaning device 10. The enclosure structure may be at least within one or both of first hand-placement structure 12 and second hand-placement structure 14. In one implementation, during operation of hand cleaning device 10, such as depicted in FIG. 2, cleaning agent is released through one or more outlets (20a and 20b).

In one embodiment, and as depicted FIG. 2, when cleaning device 10 is in-use, a user's first hand 36 may be positioned on a first hand-placement structure 12, and/or a second hand 38 of the same user may be positioned on a second hand-placement structure 14. As shown in the illustrative embodiment of FIG. 2, a first palm (not shown due to facing away from the viewer of the drawing) of said first hand 36 faces towards a second palm (not shown) of said second hand 38. As such, during operation, hand cleaning device 10 may release a cleaning agent onto one or more of said first palm and said second palm of a user's first hand 36 and second hand 38, respectively, and through one or more outlets 20a and 20b. Additionally, cleaning device 10 may release a cleaning agent through one or more interior outlets (not shown), wherein an interior outlet may be positioned within a cavity, such as a cavity aligned with an opening (16a-16f and 18a-18b). As such, and as described throughout this disclosure, hand cleaning device 10 may release a cleaning agent onto one or more palms of a user, and wherein it is assumed that by releasing the cleaning agent onto a palm of a hand, a user may subsequently spread said cleaning agent across one or more palms, fingers, thumbs, backs of the respective user's hands, and onto one or more wrist areas of the user, by, among others, subsequently rubbing one or more hands together.

As previously described, during operation of cleaning device 10, a user may position a first hand 36 on a first hand-placement surface 22, and a second hand 38 on a second hand-placement surface 24. In one implementation, upon positioning of one or more of said first hand 36 and said second hand 38, a cleaning agent may be released through one or more exterior outlets (20a and 20b), or interior outlets. Example interior outlets are described below in at least in relation to FIGS. 5-7.

As depicted in the embodiment of FIG. 1, cleaning device 10 may comprise an axis of rotation 34. In one implementation, the first hand-placement structure 12 is rotatably coupled to the second hand-placement structure 14 by one or more of, a bearing, a mechanical gear mechanism, or by a coupling comprised of a flexible material that allows for a range of motion, including a rotational/twisting motion, among others. In one implementation, the first-hand-placement structure 12 may be displaced relative to the second hand-placement structure 14 by a predetermined amount, wherein said predetermined amount may be a predetermined length. In one embodiment, the predetermined length may be, among others, less than 1 cm, less than 2 cm, or less than 5 cm, and the like. Those skilled in the art will realize that these are merely example lengths and the disclosure is not limited to such distances.

In certain implementations, the first hand-placement structure 12 and the second hand-placement structure 14 may rotate in opposite directions about axis 34, as indicated by arrows 30 and 32 respectively. In one implementation, said first hand-placement structure 12 may rotate freely relative to said second hand-placement structure 14. In another implementation, the range of motion of said first-hand-placement structure 12 relative to said second hand-placement structure 14 is limited to a predetermined angle, and wherein said predetermined angle may be, among others, about or less than 360°, less than 180°, or less than 120°, or other angles, such as 90 degrees or less than 90 degrees. In another implementation, however, the first hand-placement structure 12 may be rigidly coupled to the second hand-placement structure 14.

Additionally, and as depicted in FIG. 2 by arrows 68 and 70, during certain envisioned operations of hand cleaning device 10, a user may move one or more fingers (42a-42f) and/or thumbs (40a-40b) into respective openings (16a-16f and 18a-18b) of the device 10. (If openings are not present, such as if face 50 is at least partially absent, users may move fingers or thumbs into respective cavities or form cavities). In this exemplary embodiment of FIG. 2, arrow 68 represents a first thumb 40b being moved into and out from opening 18b. This may occur as the user moves a first hand 36 in a rotational motion, as indicated by arrow 30. Accordingly, arrow 68 may be aligned with a first radial direction of cleaning device 10. Similarly, arrow 70 represents a motion of a second thumb 40a into and out from opening 18a as said user simultaneously rotates a second hand 38 in a direction indicated by arrow 32. Furthermore, arrow 70 may be aligned with a second radial direction of cleaning device 10.

As a user moves a finger and/or any digit into and out of an opening or cavity, such as for example, as indicated by arrows 68 and 70, said finger and/or digit may contact one or more surfaces of a cavity. In this way, contact between said moving finger and/or thumb and the one or more surfaces of a cavity, may serve to reduce a level of infectious agents on said finger and/or thumb. In one implementation, device 10, or one or more of device 70 depicted in FIG. 3, device 100, depicted in FIG. 4, device 140 depicted in FIG. 6, device 220 depicted in FIG. 8, device 300 depicted in FIG. 9, or device 63 depicted in FIG. 10 may reduce a level of infectious agents present on a one or more areas of skin of a user (those areas of skin including, among others, one or more of a finger, thumb, toe, palm, or any other area of skin associated with a hand or a foot of a user). In one configuration, one or more of devices 10, 63, 70, 100, 140, 220, and/or 300, or combinations or equivalents thereof, may reduce a level of infectious agents on an area of skin, or within wounded cut or graze of a user, and by an amount corresponding to one or more of a slight reduction, a substantial reduction, or an elimination of infectious agents. Accordingly, a slight reduction in a level of infectious agents may be at least a 10% reduction, and the like. A substantial reduction may be at least a 50% reduction, and the like. An elimination may be at least a 95% reduction. Additionally or alternatively, one or more of devices 10, 63, 70, 100, 140, 220, and/or 300 may prevent transmission of an infectious agent between two areas of skin associated with a same user (e.g. between two digits of a user), and/or between two users. Furthermore, it will be readily understood to those of skill in the art that one or more of devices 10, 63, 70, 100, 140, 220, and/or 300, or combinations or equivalents thereof may reduce a level of infectious agents on an area of skin by removing the infectious agents from the skin, and/or by ameliorating the infectious aspects of the infectious agents while leaving part or all of the material associated with the agents in situ on an area of skin of a user. For example, one or more of the devices described in this disclosure may kill bacteria or viruses, and the like, but some or all of the matter may remain on an area of skin of the user without the potential transmit one or more diseases to the user or other individuals.

In another implementation, one or more fingers (42a-42f) and/or thumbs (40a-40b) may be moved into and out from device 10 through one or more respective openings (16a-16f and 18a-18b) without rotational motion of device 10 about axis 34.

In one implementation, divider structure 26 (shown in FIG. 1) may comprise a coupling between the first hand-placement structure 12 and the second hand-placement structure 14. Additionally or alternatively, divider structure 26 may comprise any material for reducing or eliminating transmission of one or more infectious agents between said first hand-placement structure 12 and said second hand-placement structure 14.

In yet another implementation, a cleaning agent may be released from cleaning device 10 onto one or more palms, fingers, or thumbs of one or more hands of a user upon, among others, insertion of one or more fingers and/or thumbs into one or more openings (16a-16f and 18a-18b) on said device 10, positioning of one or more of first hand 36 or second hand 38 onto device 10, or rotating the first hand-placement structure 12 relative to the second hand-placement structure 14 about an axis, e.g., axis 34. Accordingly, in one implementation, hand cleaning device 10 may comprise a material that encapsulates the hand cleaning agent. For example, hand cleaning device 10 may comprise one or more sponge-like materials, and wherein a cleaning agent may be contained within said one or more sponge-like materials. In another implementation, a hand cleaning agent may be encapsulated within a reservoir within hand cleaning device 10. In certain embodiments, the reservoir may be identical or similar to reservoirs 120, and 128 of the example embodiment shown in FIG. 5. In yet another implementation, hand cleaning device 10 may be manufactured without a cleaning agent, and/or a cleaning agent may be introduced onto/into cleaning device 10 during use.

Figure 3:
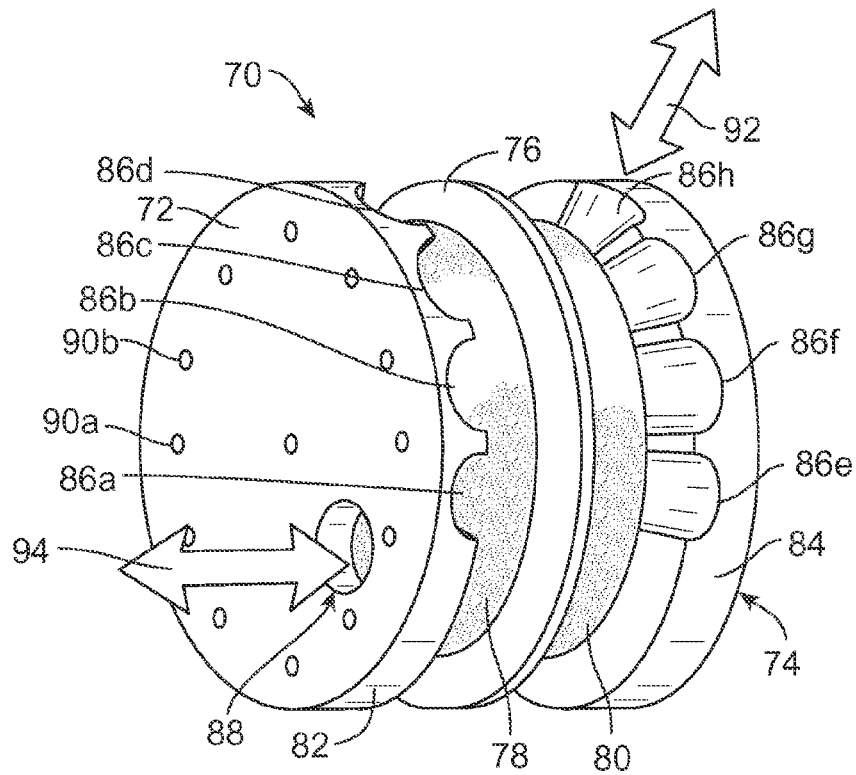
FIG. 3 depicts another example of a hand cleaning device in accordance with one illustrative embodiment.

FIG. 3 depicts an alternative embodiment of a hand cleaning device 70. In particular, hand cleaning device 70 includes a first hand-placement structure 82 with a first hand-placement surface 72, a second hand-placement structure 84 with a second hand-placement surface 74 (not shown), a divider structure 76, a first channel 78, a second channel 80, a plurality of outlets (represented by outlets 90a-90b), alignment structures 86a-86h, and opening 88. In one implementation, cleaning device 70 may be similar to clean device 10 from FIG. 1 in one or more aspects and/or comprise one or more materials including, among others, polymers, fiber-reinforced polymers, metals, alloys, ceramics, plant material (for example, would, or cellulose wood fibers, and the like), natural sponges, synthetic materials that exhibit one or more properties of high compressibility, high absorbency, or texture with abrasive qualities suitable for scrubbing skin (synthetic sponges), or combinations thereof.

Similarly to cleaning device 10 from FIG. 1, the first hand-placement structure 82 of device 70 may, in certain embodiments, be coupled to the second hand-placement structure 84 by a rigid coupling, a rotatable coupling, or a flexible coupling, and such that the first hand-placement structure 82 may move relative to the second hand-placement structure 84.

In one implementation, cleaning device 70 may release a cleaning agent from one or more of outlets 90a-90b, and wherein outlets 90a-90b may represent a plurality of outlets, or alternatively, a single outlet, on the first hand-placement surface 72. Additionally, it will be readily apparent to those of skill that the pattern of outlets 90a-90b is merely one of a plurality of different patterns of outlets of outlets (90a-90b) on the first hand-placement surface 72 that are conceivable without departing from the scope of this disclosure.

In another implementation, hand cleaning device 70 may comprise a divider structure 76 separating the first hand-placement structure 82 from the second hand-placement structure 84. The divider structure 76 may comprise one or more of an impermeable material, or a semipermeable, or a permeable material, such that divider structure 76 is configured to reduce or eliminate transmission or migration of one or more infectious agents between the first hand-placement structure 82 and the second hand-placement structure 84.

The illustrated example of hand cleaning device 70 is shown with a first channel 78 and a second channel 80.

Accordingly, in one example, a user may insert one or more fingers and/or thumbs into the first channel 78 and the second channel 80 in order to reduce or prevent a level of infectious agents present on one or more hands and specifically, on one or more distal digits, of the user. In one implementation, the first hand-placement structure 82 comprises a plurality of alignment structures 86a-86d, wherein a hand alignment structure 86a-86d may comprise a groove in a sidewall of the first hand-placement structure 82. Accordingly, the plurality of alignment structures 86a-86d may promote separation of one or more digits, e.g., fingers, toes and/or thumbs of a user. Additionally, it will be readily apparent to those of skill that the depicted four alignment structures 86a-86d may represent a plurality of alignment structures less than, or greater than those four depicted. In one embodiment, an alignment structure (86a-86d) may promote/encourage a separation distance between two adjacent digits of a user such that transmission of one or more infectious agents between a first digit and a second digit is reduced or eliminated. Furthermore, it will be readily apparent to those of skill that the second hand-placement structure 84 may operate in a similar manner to the first-hand-placement structure 82.

Similar to hand cleaning device 10 from FIG. 2, a user may periodically insert and remove one or more fingers and/or thumbs into and out from channel, such as channel 78 or channel 80. In one implementation, a finger and/or any digit aligned with alignment structure 86h may move into an out from channel 80 along radial direction 92. In another implementation, hand cleaning device 70 includes an opening 88 for receiving a thumb or any digit of a user. Accordingly, opening 88 may provide for an ergonomic grip of hand cleaning device 70. As such, a user may periodically insert and remove any digit into and out from opening 88 in order to reduce a level of infectious agents on the skin of any digit, and in a substantially axial direction indicated by arrow 94.

In one embodiment, a user may operate hand cleaning device 70 by positioning a left hand on the first hand-placement surface 72 and a right hand on the second hand-placement surface 74. As such, in one example, one or more fingers of the user's left hand may be aligned with respective alignment structures 86a-86d, and the user's left thumb may be aligned with opening 88. Furthermore, when positioned on the first hand-placement surface 72 and the second hand-placement surface 74, a palm of a user's left hand faces towards a palm of said user's right hand. Additionally, as a user moves one or more fingers and/or thumbs into the first channel 78, the second channel 80, or opening 88, one or more surfaces/areas of skin of one or more respective fingers and/or thumbs of the user may contact one or more surfaces of the cleaning device 70, and thereby reducing or eliminating a level of infectious agents on the respective areas of skin.

Figure 4:
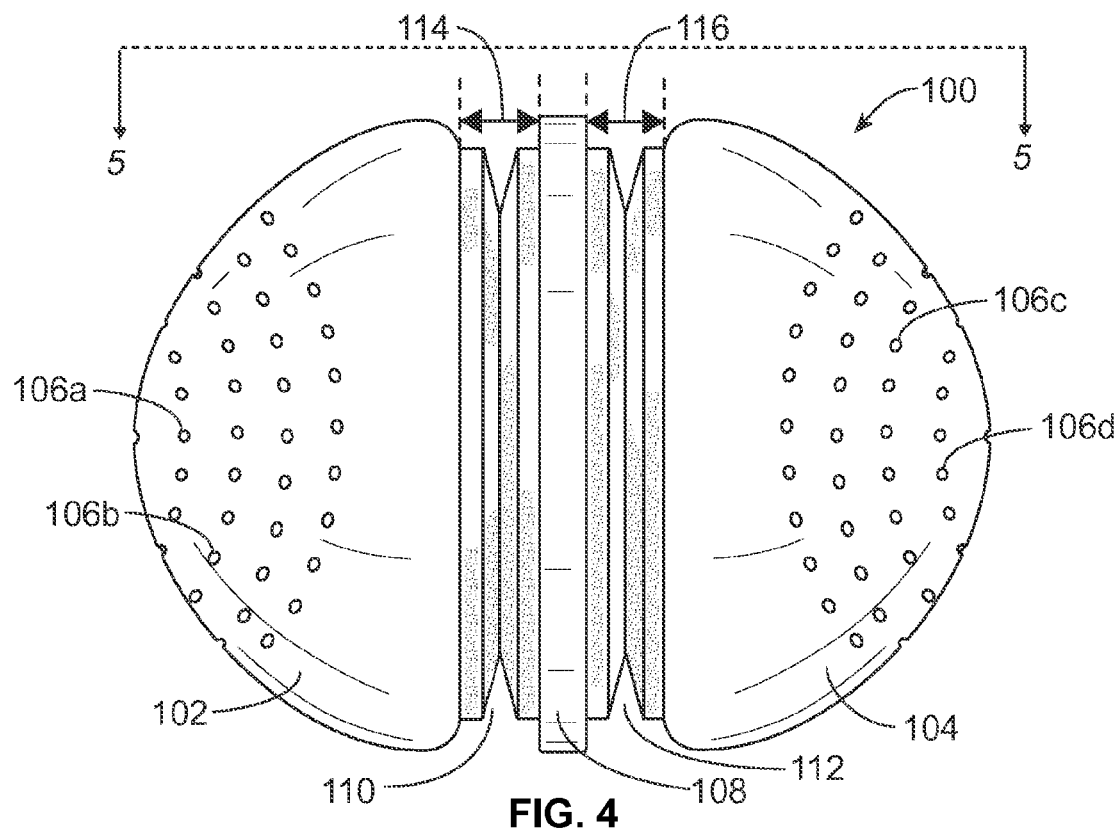
FIG. 4 depicts a different hand cleaning device in accordance with one illustrative embodiment.

FIG. 4 depicts another embodiment of a hand cleaning device—device 100. In particular, hand cleaning device 100 includes a first hand-placement structure 102, a second hand-placement structure 104, a plurality of outlets 106a-106d, a divider structure 108, a first channel 110, and a second channel 112. In one implementation, hand cleaning device 100 may operate in a similar manner to hand cleaning device 10 shown in FIG. 1 and/or hand cleaning device 70 shown in FIG. 3. As such, hand cleaning device 100 may reduce or eliminate a level of infectious agents on one or more areas of skin of the user by bringing one or more fingers, thumbs, or other areas of one or more hands of the user into contact with one or more cleaning surfaces of cleaning device 100, or a cleaning agent. For example, a user may position a first hand on first hand-placement structure 102, and a second hand on the second hand-placement structure 104. Accordingly, a user may insert one or more fingers and/or thumbs of said first-hand into the first channel 110 and similarly, one or more fingers and/or thumbs of said second hand into the second channel 112. Also, finger grooves or guides (and/or other structures), which in one embodiment may appear on the hand-placement structures, may be configured to facilitate cleaning of those often neglected areas between one or more digits.

In one implementation, upon insertion of one or more fingers and/or thumbs into the first channel 110 and/or the second channel 112, said inserted fingers and/or thumbs may come and contact with a cleaning agent released from one or more outlets (not shown), or one or more cleaning surfaces of cleaning device 100. For example, the first channel 110, and the second channel 112 may comprise one or more materials configured to contact an area of skin in order to reduce the level of infectious agents present on said area of skin. In this way, the first channel 110, and the second channel 112 may comprise one or more materials with abrasive properties, antibacterial properties, hypoallergenic properties, and/or absorbent properties configured to clean the skin of a user.

In one implementation outlets 106a-106d are configured to release a cleaning agent onto the one or more palms of a user for reducing a level of infectious agents on a surface area of skin associated with one or more hands of the user. In another implementation, the first channel 110 on the second channel 112 are configured with respective widths 114 and 116 that are less than a thickness of one or more fingers and/or thumbs of the user. As such, deformation of a material (such as for example compression of sponge-like material) may occur upon insertion of a finger and/or thumb into one or more of the first channel 110 or the second channel 112, wherein said deformation increases a surface area of cleaning device 100 in contact with a surface area of one or more fingers and/or thumbs of a user.

The example hand cleaning device 100 from FIG. 4 is depicted with a substantially spherical shape. In one implementation, cleaning device 100 partially or wholly comprises a deformable (sponge-like) material. As such, in one embodiment, hand cleaning device 100 may be stored in a compressed state/configuration (stored at a pressure less than ambient pressure and/or under compressive forces) within a retaining structure, such as for example wrapper material (not shown) such that the volume of hand cleaning device 100 is reduced during storage. For example, hand cleaning device 100 may be stored in a compressed state with a shape that is substantially cylindrical, for example, such as similar to hand cleaning device 70 from FIG. 3. Accordingly, upon opening of hand cleaning device 100, a compressed shape may expand into an uncompressed shape at an ambient pressure or upon less compressive forces (such as, for example, a standard atmospheric pressure of 101.325 kPa), such as that substantially spherical shape depicted in FIG. 4. In one embodiment, a twisting or rotational force may cause the structure to expand from compressed state to an expanded state. In certain embodiments, this may be configured to occur without the need for a retaining structure. Twisting and/or rotational forces may also cause the release of agents.

Figure 5:
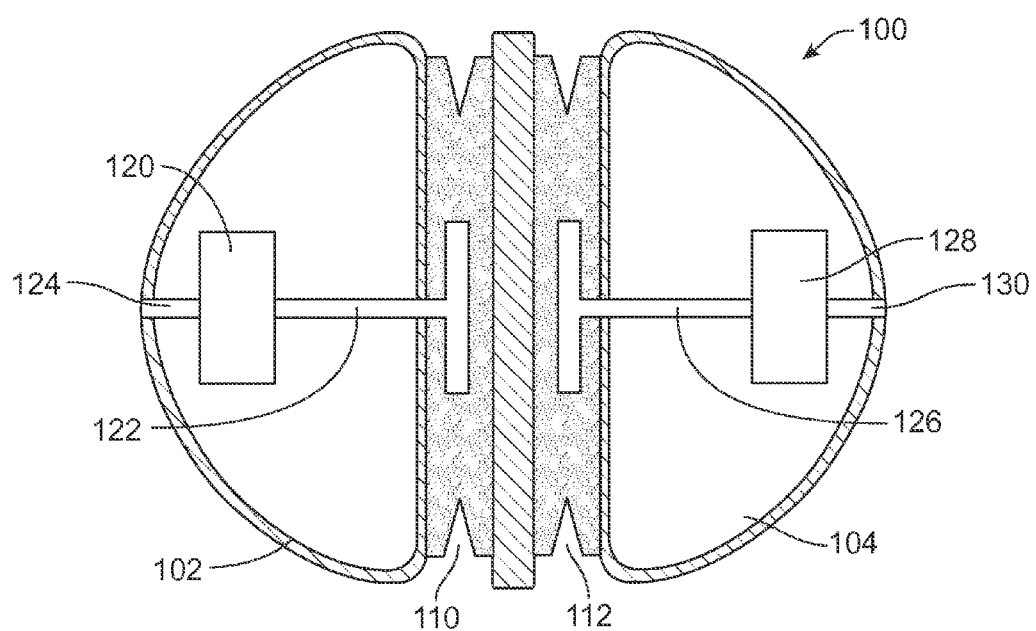
FIG. 5 schematically depicts a cross-sectional view of an example implementation of the hand cleaning device of FIG. 4 in accordance with one illustrative embodiment.

FIG. 5 schematically depicts a cross-sectional view of an example hand cleaning device, such as for example, device 100 shown in FIG. 4. In particular, FIG. 5 depicts an internal view of an example first hand-placement structure 102, the second hand-placement structure 104, the first channel 110, and the second channel 112. Additionally, FIG. 5 depicts a first reservoir 120, a first external duct 124, a first internal duct 122, a second external duct 130, and a second internal duct 126.

In one implementation, the first reservoir 120 and the second reservoir 128 may encapsulate a cleaning agent, such as one or more of those previously described. As such, the first reservoir 120 and the second reservoir 128 may be agent-filled capsules. In an alternative embodiment, however, reservoirs 120 and 128 may represent a mass of cleaning agent encapsulated within the first hand-placement structure 102 and the second hand-placement structure 104, wherein said structures 102 and 104 comprise one or more absorbent materials, and a cleaning agent is retained within said one or more absorbent materials. Thus, the structure itself comprises the reservoir.

In one embodiment, the first reservoir 120 and/or the second reservoir 128 may release a cleaning agent into one or more of the first external duct 124, the first internal duct 122, the second external duct 130, or the second internal duct 126. As such, ducts 122, 124, 126, and 130 may comprise, among others one or more tubes within hand cleaning device 100, and/or may represent one or more pores of a porous material through which a cleaning agent may permeate. Accordingly, said first external duct 124 and said second external duct 130 may release one or more cleaning agents through one or more of a plurality of outlets, such as those outlets represented by outlets 106a-106d in FIG. 4. Similarly, said first internal duct 122 and said second internal duct 126 may release a cleaning agent into the first channel 110 and the second channel 112, respectively, through one or more outlets (not shown).

Additionally, the first reservoir 120 and the second reservoir 128 may release one or more cleaning agents through one or more of ducts 122, 124, 126, and/or 130 as a result of, among others, rotation of the first hand-placement structure 102 relative to the second hand-placement structure 104 (e.g., about an axis of rotation similar to axis of rotation 34 from FIG. 1 and cleaning device 10). As such, rotation of the first-hand-placement structure 102 relative to the second hand-placement structure 104 may engage one or more release mechanisms to force a cleaning agent through one or more of ducts 122, 124, 126, and/or 130. Additionally, hand cleaning device 100 may release one or more cleaning agents onto one or more areas of a hand of a user (fingers, thumbs, palms, and the like) as a result of contact between a first and/or a second hand, and hand cleaning device 100. In this way, hand cleaning device 100 may comprise one or more sponge-like materials in which one or more cleaning agents are encapsulated (as previously described), and a user may deform (compress/squeeze) hand cleaning device 100 in order to release one or more cleaning agents. Additionally, and cleaning device 100 may comprise one or more masses of cleaning agent encapsulated within one or more reservoirs (120, 130), wherein said one or more reservoirs are ruptured, and subsequently release the encapsulated cleaning agent upon operation of hand cleaning device 100. For example, the hand cleaning device 100 may comprise one or more capsules of cleaning agent, and said one or more capsules of cleaning agent may be ruptured (releasing the cleaning agent) as a user compresses/twists the first hand-placement structure 102 and the second hand-placement structure 104 with one or more hands.

Figure 6:
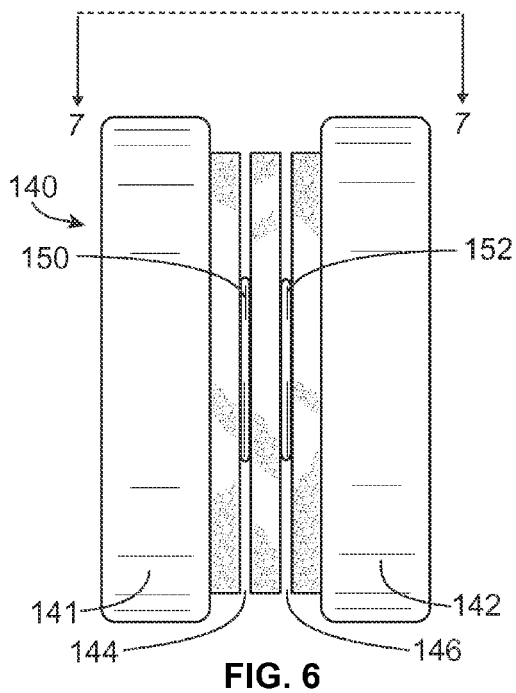
FIG. 6 depicts yet another implementation of an example hand cleaning device in accordance with one illustrative embodiment.

FIG. 6 depicts yet another embodiment of an example hand cleaning device—device 140. However, the operation and construction of hand cleaning device 140 may be similar to hand cleaning device 10 from FIG. 1, and hand cleaning device 70 from FIG. 3, and/or hand cleaning device 100 from FIG. 4. Accordingly, hand cleaning device 140 includes a first hand-placement structure 141, a second hand-placement structure 142, a first channel 144, a second channel 146, a first lip structure 150, and a second lip structure 152. Accordingly, in one implementation, FIG. 6 depicts an end view of said hand cleaning device 140, wherein hand cleaning device 140 may comprise a substantially cylindrical shape.

In one embodiment, a user may operate hand cleaning device 140 by periodically inserting and removing one or more fingers and/or thumbs into and out from the first channel 144 and/or the second channel 146. In one implementation, hand cleaning device 114 may release a cleaning agent into said first channel 144 and said second channel 146 upon insertion of one or more fingers and/or thumbs, wherein the cleaning agent may reduce or eliminate a level of infectious agents present on one or more areas of skin of the one or more inserted fingers and/or thumbs, and in particular, reduce or eliminate a level of infectious agents present on an area of skin on one or more distal aspects of one or more fingers and/or thumbs.

In certain implementations, the first lip structure 150 and the second lip structure 152 may be configured such that during usage of the device, there is an increased surface area of hyponychium skin that is exposed to a cleaning agent. Specifically, the first lip structure 150 and the second lip structure 152 may increase a surface area of hyponychium skin that is exposed to the cleaning agent between a free margin and an onychodermal band of a finger or any digit, thereby reducing a level of infectious agents present on said area of hyponychium skin. Example embodiments are further described in relation to FIG. 11A and FIG. 11B. In another configuration, a lip structure may be formed in a hand cleaning device upon insertion of one or more digits into the device. Accordingly, said device may comprise one or more compressible and/or deformable materials. Upon insertion of one or more digits, the materials may conform to a shape of the one or more digits, and contact one or more areas of skin close to, and/or under a nail of the user. Accordingly, the one or more materials may contact an area of hyponychium skin, and/or one or more other areas of skin close to a nail of a user. Additionally or alternatively, the one or more materials from which a hand cleaning device is constructed may have one or more differing properties of rigidity, compressibility, and/or density such that, upon insertion of a digit of the user into the device, a lip structure is formed around the digit with a structure similar to that of lip structure 150 and/or 152.

Figure 7:
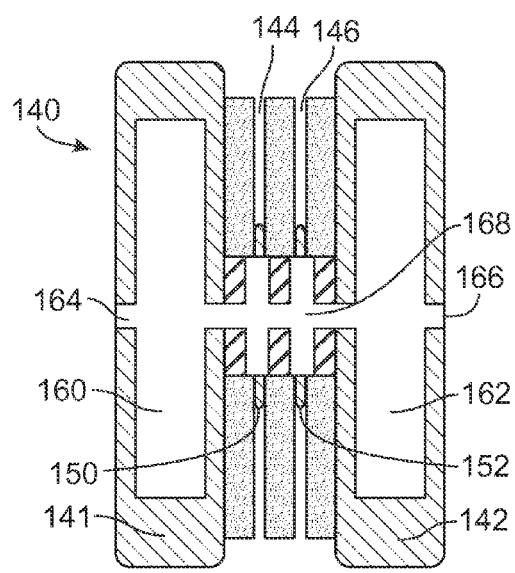
FIG. 7 schematically depicts a cross-sectional sectional view of an example implementation of the hand cleaning device of FIG. 6 in accordance with one illustrative embodiment.

FIG. 7 schematically depicts a cross-sectional view of a hand cleaning device, which may be device 140 from FIG. 6 in certain embodiments. Accordingly, FIG. 7 depicts the first hand-placement structure 141, the second hand-placement structure 142, the first channel 144, the second channel 146, the first lip structure 150, and the second lip structure 152. Additionally, FIG. 7 depicts a first reservoir 160, a second reservoir 162, a first exterior outlet 164, a second exterior outlet, and interior outlet system 168. Similarly to FIG. 5, the first reservoir 160 and the second reservoir 162 may represent elements for encapsulating one or more cleaning agents. Additionally or alternatively, the first and the second reservoirs 160 and 162, respectively, may represent a mass of cleaning agent encapsulated within a material, such as a porous, absorbent, sponge-like material. Furthermore, it will be readily apparent to those of skill that hand cleaning device 140 may alternatively be embodied with a single reservoir, or a plurality of reservoirs in excess of the two reservoirs (160, 162) depicted in FIG. 7.

Exterior outlets 164 and 166 may be similar to exterior outlets 124 and 130 from FIG. 5, wherein exterior outlets 164 and 166 may facilitate release of one or more cleaning agents onto one or more palms of a user. Similarly, interior outlet system 168 may represent one or more conduits for release of one or more cleaning agents into the first channel 144 and the second channel 146 for contact with one or more digits of a user. In another implementation, however, interior outlet system 168 may represent one or more pores of a porous material encapsulating one or more cleaning agents, and wherein the encapsulated one or more cleaning agents may be released onto one or more digits, e.g., fingers toes and/or thumbs of a user upon contact of the porous material with said fingers, toes and/or thumbs.

Figure 8:
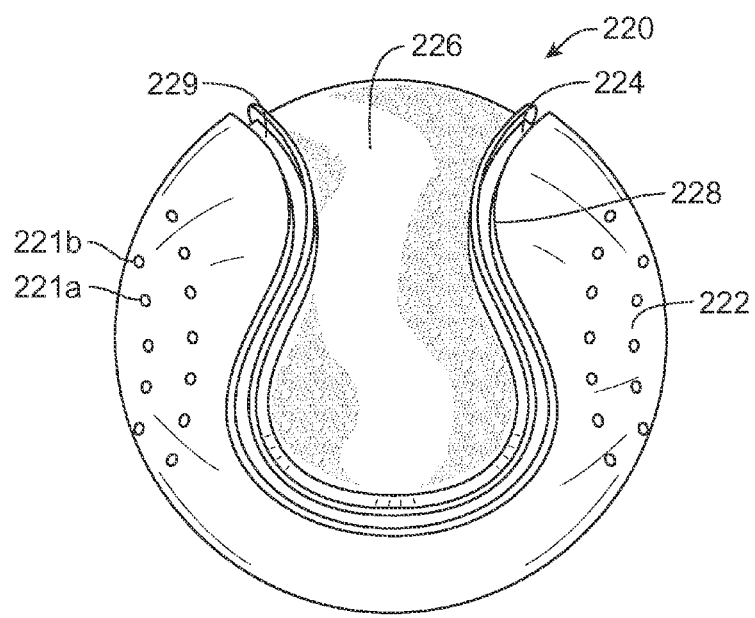
FIG. 8 depicts yet another implementation of an example hand cleaning device in accordance with one illustrative embodiment.

FIG. 8 depicts another embodiment of a hand cleaning device 220. As such, FIG. 8 depicts a substantially spherical hand cleaning device 220 having outlets 221a-221b, a first surface 222, a lip structure 224, a second surface 226, a seam 228, and a cleaning surface 229. In one implementation, a user may grip hand cleaning device 220 with one or more hands positioned on the first surface 222. Accordingly, a user may position one or more distal aspects of one or more digits, e.g., fingers, toes and/or thumbs across seam 228. In this way, hand cleaning device 220 is configured with seam 228 similar to a sports ball, and accordingly, may be gripped similarly to how a user would grip a sports ball, such as a baseball, a softball, or a tennis ball, among others. Accordingly, hand cleaning device 220 may have a diameter measuring approximately 75 mm, and other dimensions of balls and/or other sporting objects generally used.

In one implementation, hand cleaning device 220 may comprise a plurality of outlets, represented by outlets 221a-221b, which may be similar to outlets 20a-20b shown in FIG. 1. Accordingly, hand cleaning device 220 may encapsulate a mass of cleaning agent within the device, for release through the plurality of outlets 221a-221b. In another implementation, the second surface 226 may comprise a material with abrasive properties for scrubbing one or more areas of one or more hands of the user, and thereby reducing a level of infectious agents present on a user's hands. In another implementation, a user may position one or more digits, e.g., fingers, toes and/or thumbs on an optional lip structure 224, wherein lip structure 224 may be similar to lip structure 210 from FIG. 11B in certain embodiments. Additionally or alternatively, cleaning device 220 may comprise one or more materials that exhibit compressibility such that a user may deform one or more of the first surface 224 and the second surface 226 by periodically moving one or more digits into and out from one or more of said surfaces 222 and 226 and/or cleaning surface 229. Furthermore, a user may move one or more fingers and/or thumbs back and forth along seam 228, thereby bringing one or more areas of the user's hands into contact with cleaning surfaces (222 and 226) of cleaning device 220.

Figure 9A:
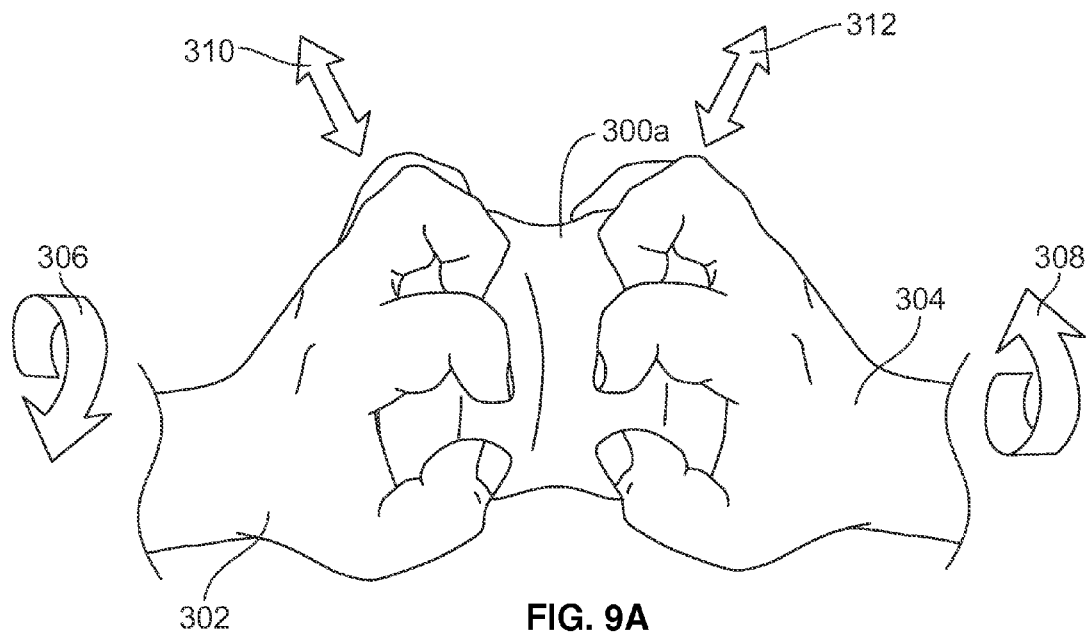
FIG. 9A-9G schematically depict a plurality of stages of degradation/decomposition of another example implementation of a hand cleaning device in accordance with one illustrative embodiment.

FIG. 9A-9G schematically depict a plurality of stages of degradation/decomposition of another embodiment of a hand cleaning device—device 300. In particular, FIG. 9A depicts a first hand 302 and a second hand 304 in contact with hand cleaning device 300, wherein hand cleaning device 300 is in a first, fully-formed configuration, represented by configuration 300A.

In one implementation, hand cleaning device 300 may comprise one or more similar materials or properties to one or more of hand cleaning device 10 from FIG. 1, hand cleaning device 70 from FIG. 3, hand cleaning device 100 from FIG. 4, and hand cleaning device 140 from FIG. 6. In one embodiment, hand cleaning device 300 may comprise a degradable material such as, among others, melamine foam. Accordingly, hand cleaning device 300 may chemically and/or physically breakdown during one or more processes to clean one or more hands of a user. As such, hand cleaning device 300 may comprise a material that breaks down at a rate that is similar to a time for thorough cleaning of one or more hands of a user. In one implementation, this degradable material may breakdown after approximately 30 seconds, one minute, or two minutes, and/or other time frames of contact with one or more hands of the user. The density and/or material composition of the device may not be uniform in certain embodiments, thus resulting in a variable decomposition rate. A variable decomposition rate may result in a degradation profile that is configured to permit cleaning of certain areas and/or longer duration of cleaning for certain areas.

In a similar manner to the operation of cleaning devices 10, 70, 100, and 140 previously described, a user may move a first and/or a second hand (302 and/or 304, respectively) relative to cleaning device 300 by rotational motion (represented by arrows 306 and 308) and/or linear motion (represented by arrows 310 and 312). Accordingly, cleaning device 300 may breakdown as a result of exposure to an agent, such as a cleaning agent, which may be associated with or without friction between one or more fingers, thumbs, palms, and/or other areas of a user's hand with the device 300. As discussed above, those of ordinary skill in the art will understand that two or more components may be combined to form the cleaning agent; at least one component may be water to serve as a diluent; and/or water alone may serve as the cleaning agent. In one embodiment, cleaning agent may be encapsulated within an enclosure structure of hand cleaning device 10.

Figure 9B:
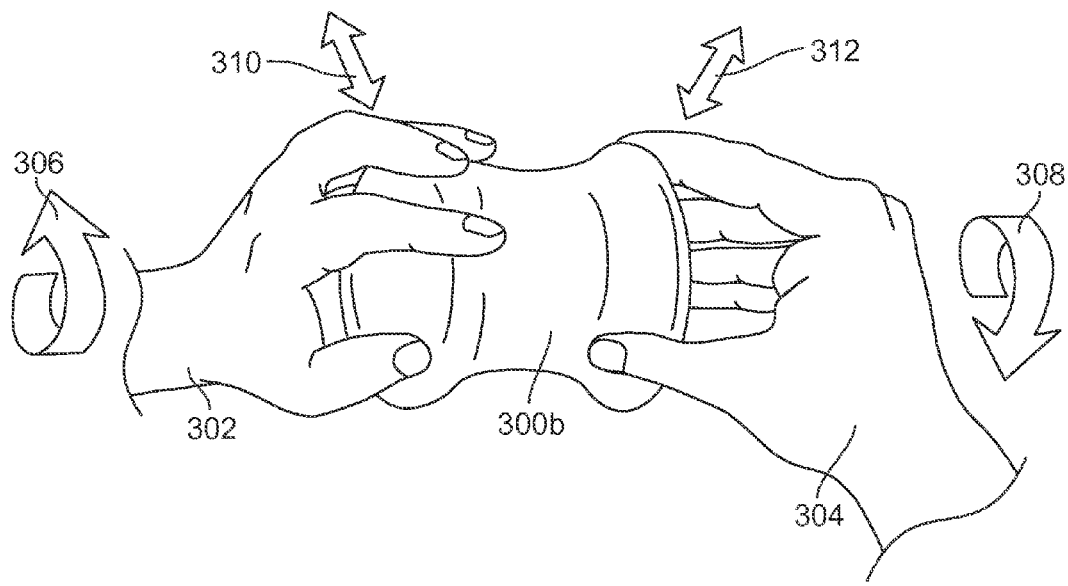
Figure 9C:
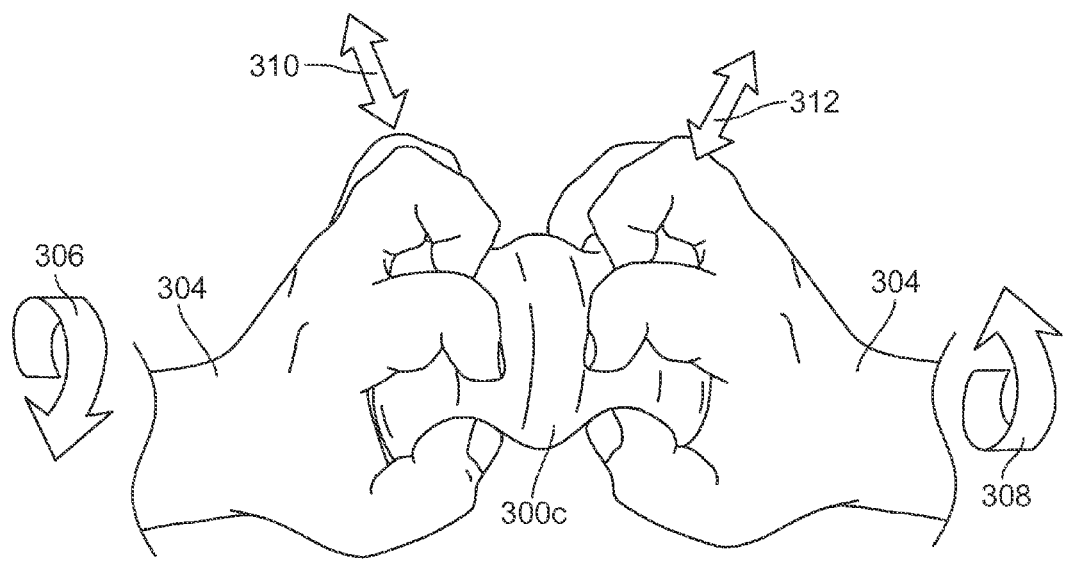
Figure 9D:
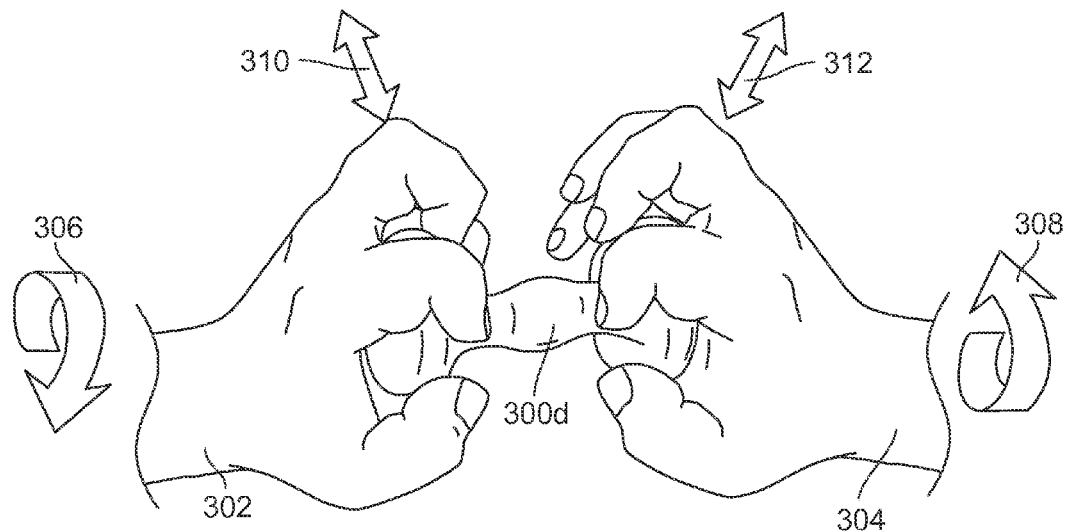
Figure 9E:
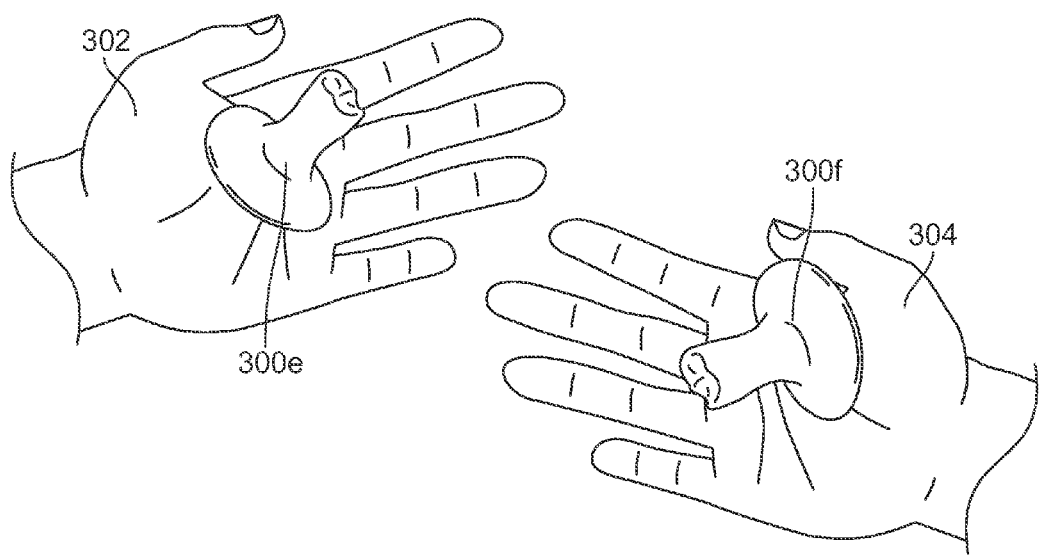
Figure 9F:
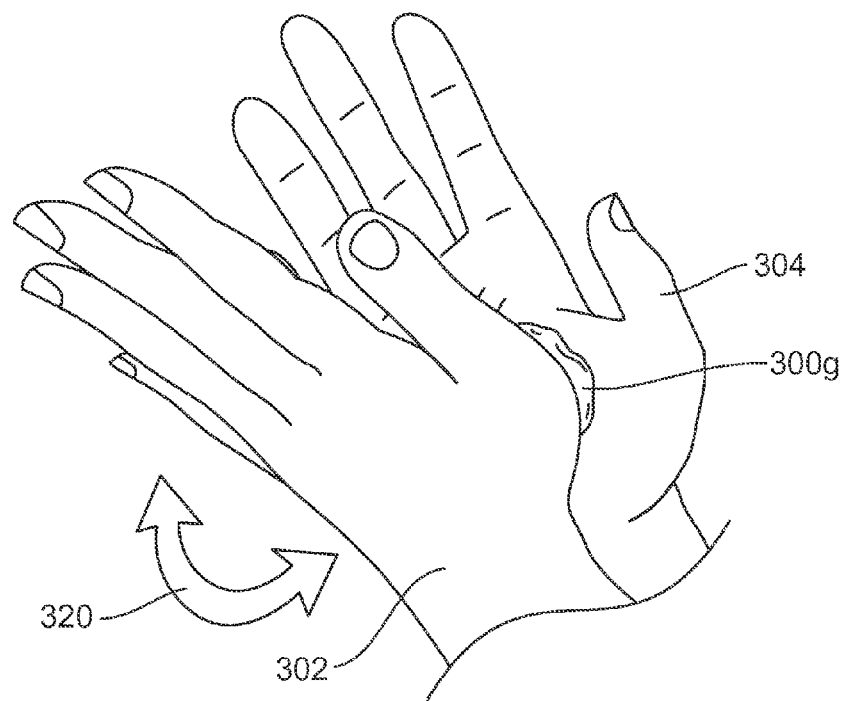
Figure 9G:
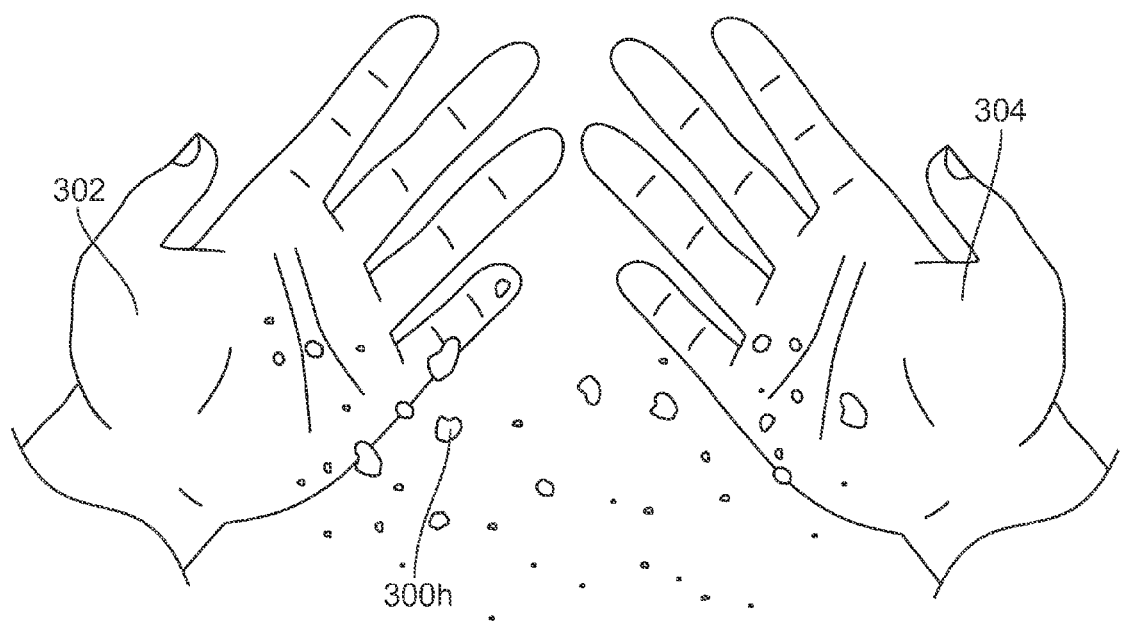

FIG. 9B depicts a second stage of degradation of hand cleaning device 300. Accordingly, hand cleaning device 300 is depicted in a configuration 300B. As one or more cleaning processes progress further, hand cleaning device 300 may breakdown/degrade into configurations similar to those depicted by configurations 300C in FIG. 9C, 300D from FIG. 9D, and 300E and 300F from FIG. 9E. Accordingly, at FIG. 9F, hand cleaning device 300 may be in a configuration similar to 300G, wherein a user may move the hand cleaning device 300 between one or more hands 302 and 304 in a circular (or otherwise) motion represented by arrow 320. As depicted in FIG. 9G, cleaning device 300 has completely broken down into a configuration represented by 300H, wherein cleaning device 300 may be wiped off of one or more hands 302 and 304 of the user. During the one or more stages of degradation of hand cleaning device 300, represented by configurations 300A, 300B, 300C, 300D, 300E, and 300F of FIG. 9A-9E, hand cleaning device 300 may reduce a level of, or eliminate, infectious agents present on one or more areas of a user's hand by bringing said areas into contact with an abrasive, antibacterial surface of hand cleaning device 300, or by releasing one or more cleaning agents on to a user's hand from hand cleaning device 300, during degradation. The cleaning agents may sterilize areas as the device breaks down and/or attenuate living organisms present in the debris.

FIG. 10 depicts a schematic cross-sectional view of a hand cleaning device—device 63. In one implementation, hand cleaning device 63 may be similar to hand cleaning device 10 from FIG. 1. In particular, hand cleaning device 63 may comprise a substantially circular cross-section 65. Accordingly, hand cleaning device 63 may be embodied with a substantially cylindrical and/or spherical shape, among others. Additionally, hand cleaning device 63 may comprise a plurality of sectors (62a-62g), wherein a sector is alternatively referred to as a cavity (62a-62g), and configured to receive one or more digits of a user, such as through an opening, such as openings 16a-16f and 18a-18b from FIG. 1, if present.

In one implementation, a cavity of cleaning device 63 may be configured with a depth dimension 66, wherein depth dimension 66 may measure at least an average length of the distal digit of the user's one or more fingers and/or thumbs. Accordingly, in one implementation, depth dimension 66 may be configured to measure an average size of a distal digit of an adult user. In another implementation, depth dimension 66 may be configured to measure an average size of a distal digit of users of variable ages. In yet another implementation, depth dimension 66 may measure at least 3.5 cm.

In one embodiment, the cross-sectional view of FIG. 10 may represent a cross-sectional view of the first hand-placement structure 12, or the second hand-placement structure 14 of cleaning device 10. As such, a cavity (62a-62g) may align with an opening 16a-16f and 18a-18b, as depicted in FIG. 1. Furthermore, while eight cavities (62a-62g) are depicted in FIG. 10, it will be readily apparent to those of skill that cleaning device 63 may be embodied with a fewer or a greater number of cavities than those depicted. For example, cleaning device 63 may be embodied with five cavities corresponding to four fingers and a thumb of one hand of a user. In one such embodiment, one cavity may have different dimensions than at least one other cavity. For example, a cavity configured to receive a thumb may be larger and/or differently shaped than a cavity intended to receive a finger.

FIG. 10 schematically depicts a divider structure 64 between cavities (62a-62g). In one implementation, divider structure 64 may comprise an impermeable material. In another implementation, divider structure may comprise a semipermeable, or a permeable material, wherein the permeability of the material is such that transmission or migration of infectious agents from a first cavity to a second adjoining cavity is longer than the time for cleaning one or more hands of a user, using cleaning device 63.

Additionally, it will be readily apparent to those of skill past cavities 62a-62g may be embodied with different shapes to those sectors depicted in the schematic cross-sectional view of FIG. 10. Accordingly, cavities 62a-62g may be embodied with a substantially rectangular, or square shapes, and the like, when viewed as a cross-section, similar to that view of FIG. 10.

Figure 11A:
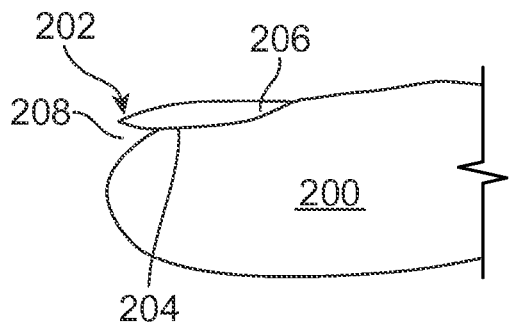
FIG. 11A-11B depicts a side view of a distal aspect of a digit of the user.
Figure 11B:
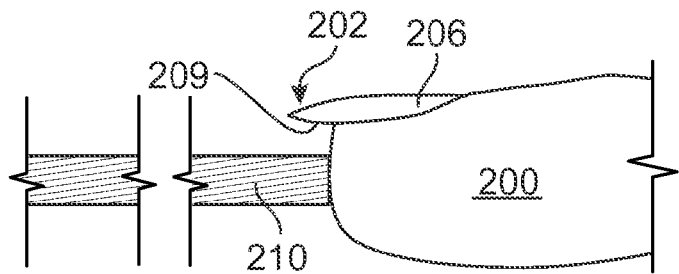

FIG. 11A depicts a side view of a distal aspect of digit 200 or any digit of a user. In particular, 11A depicts a nail plate 206 having a free margin 202, an onychodermal band 204, and a hyponychium 208 (otherwise referred to as an area of hyponychium skin 208). FIG. 11B depicts a similar side view of distal digit 200 as FIG. 11A, and further includes a lip structure 210 in contact with the distal digit 200, wherein lip structure 210 may be similar or identical to lip structures 150 and/or 152 shown in FIG. 6.

In particular, FIG. 11B depicts an increase in an area of hyponychium skin (from area 208 to an increased area 209) exposed as a result of contact between the distal digit 200 and a lip structure, such as lip structure 210. Lip structure 210 may be configured, such as through its position, size, and shape to exert a force upon at least a portion distal digit 200, thereby exposing an increased area of hyponychium skin 209. Accordingly, FIG. 11B schematically depicts a mechanism by which, among others, cleaning device 140 may reduce a level of infectious agents present on an area of skin of a user by, in one implementation, exposing an increased area of hyponychium skin to be cleaned by a cleaning device, and optionally cleaning agent from the cleaning device.

Furthermore, it will be readily apparent to those of skill that a lip structure, such as lip structure 210, may additionally or alternatively be utilized in a manner similar to a nail pick, wherein lip structure 210 may contact an underside of nail plate 206 at the free margin 202 to reduce infectious agents and/or debris underneath the nail plate 206.

Figures 12, 13:
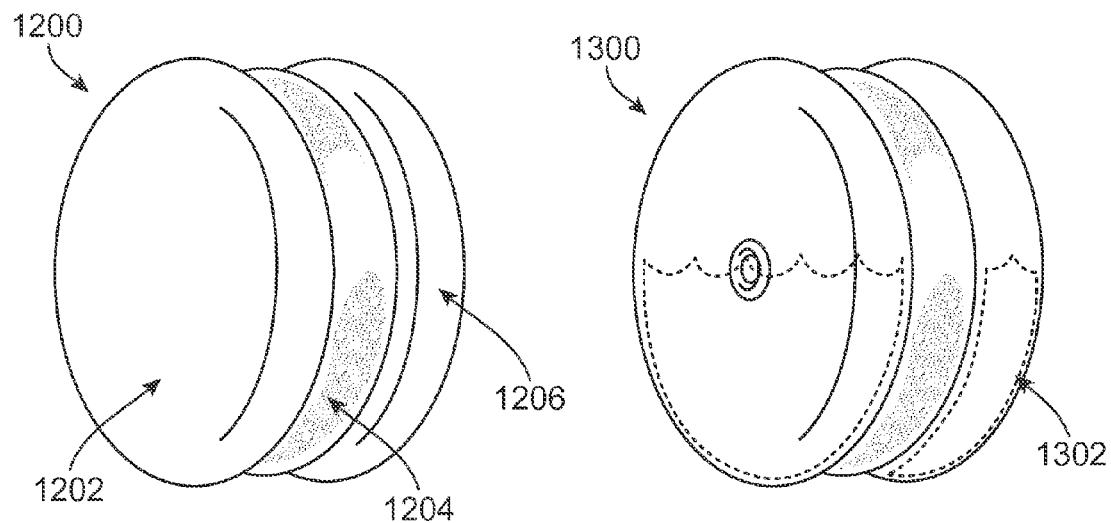
FIG. 12 schematically depicts an example implementation of a hand cleaning device in accordance with one illustrative embodiment.
FIG. 13 schematically depicts another implementation of a hand cleaning device in accordance with one illustrative embodiment.

FIG. 12 schematically depicts an alternative configuration of a hand cleaning device 1200. Hand cleaning device 1200 may comprise one or more materials and/or operating characteristics similar, or identical to one or more elements described in relation to device 10 is depicted in FIG. 1, device 70 depicted in FIG. 3, device 100, depicted in FIG. 4, device 140 depicted in FIG. 6, device 220 depicted in FIG. 8, device 300 depicted in FIG. 9, and/or device 63 depicted in FIG. 10. Accordingly, device 1200 may have a first hand-placement structure 1202 and a second hand-placement structure 1206 (which may be similar to the first hand-placement structure 12 and second hand-placement structure 14 from FIG. 1, respectively), and wherein said first hand-placement structure 1202 and said second hand-placement structure 1206 may be spaced apart, and having a channel 1204 there between (which may be similar to channel 78 or channel 80 from FIG. 3).

FIG. 13 schematically depicts an alternative implementation of a hand cleaning device 1300. In one implementation, hand cleaning device 1300 may be similar to hand cleaning device 1200 from FIG. 12. Additionally or alternatively, hand cleaning device 1300 may comprise one or more materials, elements, and/or functions described in relation to one or more of devices 10, 63, 70, 100, 140, 220, and/or 300. As depicted in FIG. 13, and cleaning device 1300 may retain a hand cleaning agent 1302, schematically depicted within hand cleaning device 1300 by dotted lines.

Figure 14:
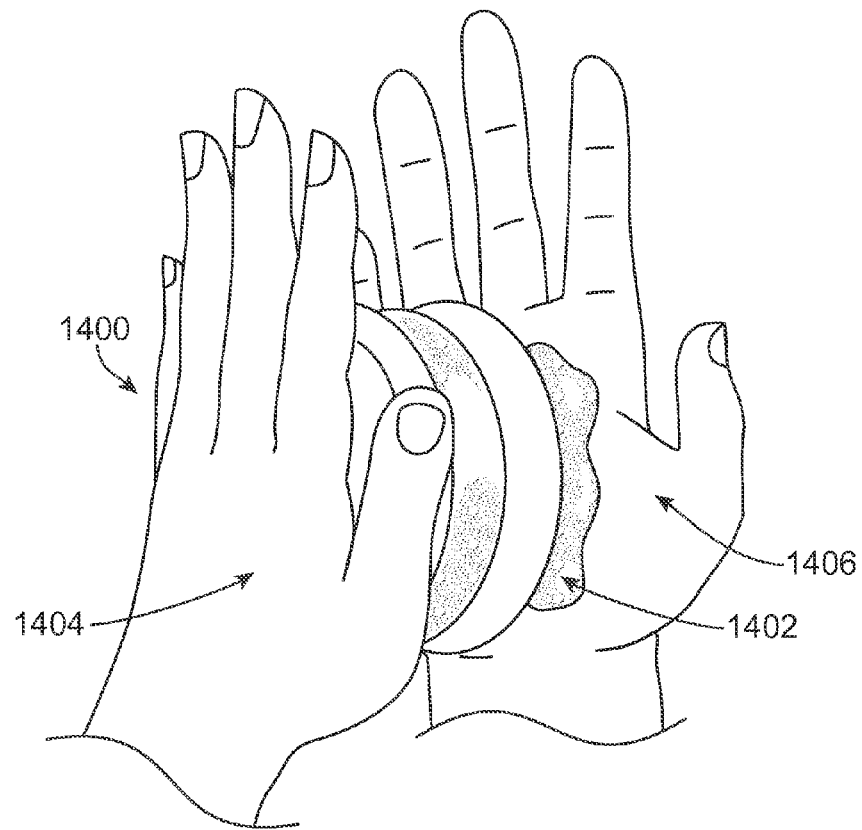
FIG. 14 depicts an implementation of a hand cleaning device in operation, and in accordance with one illustrative embodiment.

FIG. 14 schematically depicts one implementation of a hand cleaning device 1400 in operation. In particular, FIG. 14 depicts a first hand 1404 and a second hand 1406 in contact with the exemplary embodiment of a hand cleaning device 1400. Accordingly, cleaning device 1400 may be similar, or identical to one or more of hand cleaning devices 1200 and/or 1300. Additionally, cleaning device 1400 may comprise one or more elements from one or more of those devices 10, 63, 70, 100, 140, 220, and/or 300, and may release a cleaning agent onto one or more areas of skin of a user during operation, as depicted in FIG. 14 as cleaning agent 1402 is released onto the second hand 1406 of a user.

FIG. 15 schematically depicts an exemplary embodiment of a hand cleaning device 1500 in operation. Cleaning device 1500 may be similar to one or more of cleaning device 1200, 1300, and/or 1400 of FIG. 12, FIG. 13, and/or FIG. 14, respectively. In particular, FIG. 15 schematically depicts one or more digits (one exemplary digit labeled as digit 1502) being cleaned by cleaning device 1500.

FIG. 16 schematically depicts a hand cleaning device 1600. Accordingly, cleaning device 1600 may comprise one or more elements described in relation to one or more of devices 10, 63, 70, 100, 140, 220, and/or 300. Cleaning device 1600 is depicted as having a plurality of alignment structures, such as alignment structures 1604 and 1606, and which may be similar to alignment structures 86a-86h from FIG. 3. Additionally, cleaning device 1600 may have a reservoir 1602 containing a volume of a cleaning agent, wherein said reservoir, in one configuration, may have a transparent, or a partially transparent window through which an amount of cleaning agent remaining within cleaning device 1600 may be visually inspected by a user.

FIG. 17 schematically depicts an alternative implementation of a hand cleaning device 1700. Hand cleaning device 1700 may be similar to one or more of devices 10, 63, 70, 100, 140, 220, and/or 300, or combinations thereof. Accordingly, hand cleaning device 1700 may have a substantially oval shape, and/or may comprise a single deformable material, and the like. In one implementation, hand cleaning device 1700 comprises a plurality of alignment structures, wherein an alignment structure, such as that alignment structure 1702, may be configured as a dimple on a surface of hand cleaning device 1700, and configured to receive a finger tip of a user (or an end of any one or more digit of a user).

Multiple configurations of innovative cleaning devices have been disclosed. Although various configurations have been illustrated in context of certain figures or example implementations, those of ordinary skill in the art will appreciate that one or more different combinations are possible. In this regard, a device incorporating innovative aspects of this disclosure may include one or more of the following properties, which may be implemented alone or in combination with each other and/or one or more embodiments described above:

In one exemplary embodiment, a device, such as but not limited to devices 10, 63, 70, 100, 140, 220, and/or 300, may be constructed from at least partially compressible materials configured to retain or receive a cleaning agent. In yet another embodiment, the systems and methods described herein include a device configured to retain or receive a cleaning agent for expression (output) onto one or more hands of a user, or part thereof, and for atraumatic cleaning.

In another embodiment, a device, such as but not limited to devices 10, 63, 70, 100, 140, 220, and/or 300, or combinations thereof, may be configured to accept one or more digits for cleaning the digits in an atraumatic manner.

In another embodiment, devices such as but not limited to devices 70 and 100, may be configured with a single channel positioned, with respect to the horizontal axis, between the first hand-placement structure's outer surface and the second hand-placement structure's outer surface to accept one or more digits for cleaning the digits in an atraumatic manner.

In another implementation, this disclosure relates to a device that comprises pores or porous materials configured such that, upon use, allow a cleaning agent to be expressed (e.g., outputted) into a material of the device and then on to one or more hands (or part thereof) of a user. The expression of one or more agents may be into regions, channels, or areas for exposure to and cleaning of one or more digits of the user.

In another configuration, a device has regions, channels, and/or cavities that may be configured to receive one or more digits of a user, wherein the regions, channels and/or cavities are comprised of a compressible material that compresses and conforms to a shape of a one or more digits, thereby surrounding the one or more digits and one or more areas surrounding one or more nails of the user. One or more regions, channels and/or cavities may comprise of soft bristle-like materials, that essentially surround the one or more digits (or portions thereof, such as the distal digit) and/or one or more areas surrounding one or more nails of the user. Furthermore, said device conforms to a shape of one or more digits in an atraumatic manner.

In one exemplary embodiment, the systems and methods described herein include a device, such as, but not limited to, devices 10, 63, 70, 100, 140, 220, and/or 300, that has a first configuration. The device may be at a compressed state in the first configuration. In one embodiment, the device exhibits an outer perimeter having a first shape when positioned at the first configuration, which may differ from the shape of the outer perimeter when at a different (e.g., a second) configuration. As one example, the device may comprise a cylindrical and/or disk-shaped outer perimeter while at the first configuration, and a second configuration exhibits an oval or spherical shape. In certain embodiments, the device may be configured to transition from a first configuration to a second configuration, and/or vice versa, by one or more of unfolding, untwisting, and/or release of compression due to, in one example, exposure to ambient pressure, releasing agents, and/or combinations thereof.

In another embodiment, the systems and methods described herein include a barrier and/or a spacing and/or a change in material density between a pair of digits to prevent or decrease transmission of contaminated substances, such as for example, between two digits, which may be on a same hand, or on two different hands.

In one configuration, a device may comprise a degradable material. The entire device may consist of, or consist essentially of degradable material(s). The device may comprise a first degradable material configured to degrade at a first rate during normal use and a second degradable material configured to degrade at a second rate during normal use. Degradation may be influenced by time, friction, contact with one or more substances or materials and/or combinations thereof.

In another configuration, the device may comprise anti-pathogenic materials. A device may comprise, consist of or consist essentially of an intrinsically anti-pathogenic material. In one configuration, an intrinsically anti-pathogenic material may be silver, and the like.

In yet another configuration, a hand cleaning device may be substantially-comprised of an anti-pathogenic material, such as at least 90% by weight.

In yet another implementation, a cleaning agent comprises a material for substantially attenuating amount of viruses, bacteria, fungi, and the like.

In one implementation, a cleaning agent comprises a solid, a liquid, and/or a gas (including combinations thereof and/or transitional states such as foams, gels, etc). In another implementation, a cleaning agent comprises a plasma. In yet another implementation, a cleaning agent comprises a moisturizing component/material and/or a fragrance.

In one example, a cleaning agent is contained within a reservoir and released upon use of a device, such as device 10, 63, 70, 100, 140, 220, and/or 300. The cleaning device, in one example, is pre-treated with a cleaning agent, which may include premoistening the device for use upon opening, or may allow for the addition of one or more components, including but not limited to, water, either alone or with one or more agents, which may be added just prior to or at the time of use. The following clauses provide example embodiments according to various implementations:

1. A hand cleaning device, comprising:
    a device enclosure structure, further comprising:
    a first hand-placement structure; and
    a second hand-placement structure;
    a plurality of openings, wherein the plurality of openings are spaced apart on a face of the device enclosure structure;

a plurality of cavities, wherein each cavity is aligned with a respective opening, and wherein each cavity is configured to receive a digit of a user; and a barrier positioned between at least a pair of adjacent cavities and between the first and second hand placement structures, wherein the barrier comprises a material with a varying density, and said barrier is configured to substantially reduce a transmission of pathogens between adjacent cavities, as well as between the first and second hand placement structures.

2. The hand cleaning device of clause 1, further comprising a cleaning agent that is anti-pathogenic and is a liquid, dry, gaseous as well as moisturizing properties.

3. The hand cleaning device of clause 1, further comprising a cleaning agent that is anti-pathogenic and is a solid.

4. The hand cleaning device of clause 1, further comprising a cleaning agent that is anti-pathogenic and is a gas.

5. The hand cleaning device of clause 1, further comprising a cleaning agent that has one or moisturizing properties.

6. The hand cleaning device of clause 1, further comprising:
a reservoir configured to retain a cleaning agent, wherein the cleaning agent is released into a plurality of cavities and the device enclosure structure until the device is used by the user.

7. The hand cleaning device of clause 1, further comprising: a release mechanism configured to release a cleaning agent from a reservoir through one or more of a plurality of exterior and interior outlets, and into the device enclosure structure and the plurality of cavities.

8. The hand cleaning device of clause 1, wherein the release mechanism is configured to release the cleaning agent upon compressive movement of the first hand placement structure relative to the second hand placement structure.

9. The hand cleaning device of clause 1, wherein the device enclosure structure is substantially disk-like in shape.

10. The hand cleaning device of clause 1, wherein the device enclosure structure is substantially cylindrical in shape.

11. The hand cleaning device of clause 1, wherein the device comprises a com pressible material and the device has substantially cylindrical shape when in a compressed configuration, and expands into a substantially spherical shape upon activation by unfolding, untwisting, or exposure to change in ambient pressure.

12. The hand cleaning device of clause 1, wherein the device comprises intrinsically anti-pathogenic materials.

13. The hand cleaning device of clause 1, wherein an exterior outlet positioned on the face of the device enclosure structure and configured to release a cleaning agent on to a hand of the user, and an interior outlet positioned in one or more of the plurality of cavities is configured to release the cleaning agent on to one or more digits of the user.

14. The hand cleaning device of clause 1, wherein the at least one hand placement structure comprises a porous material, and wherein at least one of the plurality of exterior outlets or the plurality of interior outlets comprises pores of said porous material.

15. The hand cleaning device of clause 1, wherein the first hand placement structure is rotatably coupled to the second hand placement structure such that the first hand placement structure is configured to rotate relative to the hand placement structure by a predetermined amount or angle.

16. The hand cleaning device of clause 1, further comprising:

a lip structure within at least one cavity of the plurality of cavities, wherein a lip structure is configured such that during operation of the device, the lip structure increases a surface area of hyponychium skin that is exposed to a cleaning agent between a free margin of an onychodermal band of a digit located in the at least one cavity.

17. The hand cleaning device of clause 1, wherein the device enclosure structure comprises material configured for cleaning an area of skin of a user.

18. A hand cleaning device, comprising:
porous and compressible materials;
a first hand placement surface and a second hand placement surface configured to retain and express a cleaning agent, and to receive a first and second hand of a user;
a substantially centralized channel made of compressible material with a depth dimension of at least an average length of a distal digit, including the nail, of a user's one or more fingers and/or one or more thumbs, positioned between the first hand placement surface and second hand placement surface, the substantially centralized channel configured to receive, retain and express a cleaning agent, and to receive one or more digits of a user for atraumatic cleaning;
a reservoir configured to retain the cleaning agent until an operation of the device;
a release mechanism configured to release the cleaning agent from the reservoir, through one or more of a plurality of exterior and interior outlets, and into the at least one hand placement surface and the channel; and
an interior outlet within the channel, for releasing the cleaning agent onto one or more digits of the user.

19. The hand held device of clause 18, wherein the first and second hand placement surfaces are configured such that when the first hand of the user is positioned on the first hand placement surface and the second hand of the user is positioned on the second hand placement surface a first palm of the user's first hand faces towards a second palm of the user's second hand.

20. The hand held device of clause 18, further comprising:
a plurality of alignment structures, wherein an alignment structure, selected from the plurality of alignment structures, promotes separation of the digits of the user.

21. The hand held device of clause 18, wherein the plurality of alignment structures comprise a barrier material configured to prevent transmission of pathogens through the barrier.

22. The hand held device of clause 18, wherein the plurality of alignment structures comprise a barrier material configured to substantially decrease a transmission of pathogens through the barrier.

23. The hand held device of clause 18, wherein the device has a substantially cylindrical shape.

24. The hand held device of clause 18, wherein the device has a cylindrical shape when in a compressed configuration and expands into a substantially spherical configuration upon activation.

25. The hand cleaning device of clause 18, wherein the device itself comprises a degradable material.

26. The hand held device of clause 18, wherein the device comprises an absorbent material.

27. A hand cleaning device for reducing a level pathogens on hands and digits of the user, the device comprising:
a first hand placement area coupled to a second hand held placement area, the first and second hand placement areas being substantially symmetrical, and wherein the first hand held placement area is configured to receive a first hand of a user and the second hand placement area is configured to receive a second hand of the user such that during proper usage of the device a first palm of the first hand faces a second palm of the second hand; and a substantially centralized area comprised of porous, compressible materials and configured to receive a cleaning agent and a full length of a distal digit of the user for atraumatic cleaning 28. The device of clause 27, wherein the first hand placement area and the second hand placement area comprise a compressible material configured to receive, retain, and release a cleaning agent onto the hand and digits of the user.

29. The device of clause 27, wherein the device is spherical in shape.

30. The device of clause 27, wherein the device has a cylindrical shape and unfolds into a spherical shape.

31. A hand cleaning device, comprising:
a device enclosure structure, further comprising:
a first hand-placement structure; and
a second hand-placement structure;
a plurality of openings, wherein the plurality of openings are spaced apart on a face of the device enclosure structure;
a plurality of cavities, wherein each cavity is aligned with a respective opening, and wherein each cavity is configured to receive a digit of a user;
a barrier structure positioned between a pair of adjacent cavities, selected from the plurality of cavities, wherein the barrier structure is configured to substantially reduce transmission of an infectious agent between the pair of adjacent cavities;
an exterior outlet positioned on the face of the device enclosure structure, configured to release a cleaning fluid onto a hand of a user; and
an interior outlet positioned in one or more of the plurality of cavities, configured to release the cleaning fluid onto one or more digits of a user.

32. The hand cleaning device of clause 31, further comprising a lip structure within a at least one cavity of the plurality of cavities, wherein a lip structure is configured such that during operation of the device, to increase a surface area of hyponychium skin that is exposed to the cleaning fluid between a free margin and an onychodermal band of a finger or any digit located in the at least one cavity.

33. The hand cleaning device of clause 31, further comprising:
a cleaning fluid reservoir within the device enclosure structure configured to retain the cleaning fluid from entering the plurality of cavities until an operation of the device.

34. The hand cleaning device of clause 31, further comprising:
a release mechanism within the device enclosure structure, configured to release the cleaning fluid through one or more of the plurality of exterior and interior outlets.

35. The hand cleaning device of clause 34, wherein the release mechanism is configured to release the cleaning fluid upon movement of the first hand placement structure relative to the second hand placement structure.

36. The hand cleaning device of clause 31, wherein the at least one hand placement structure comprises a porous material, and wherein at least one of the plurality of exterior outlets or the plurality of interior outlets comprises pores of said porous material.

37. The hand cleaning device of clause 31, wherein the device enclosure structure comprises an abrasive material configured for scrubbing skin of a user.

38. The hand cleaning device of clause 31, wherein the device enclosure structure is substantially cylindrical in shape.

39. The hand cleaning device of clause 31, wherein the device comprises a compressible material, and the device has a substantially cylindrical shape when in a compressed configuration at a pressure less than an ambient pressure, and expands into a substantially spherical shape at the ambient pressure.

40. The hand cleaning device of clause 31, wherein the first hand-placement structure is rotatably coupled to the second hand-placement structure such that the first hand-placement structure is configured to rotate relative to the second hand-placement structure by a predetermined angle.

41. The hand cleaning device of clause 31, wherein the first hand-placement structure is coupled to the second hand-placement structure by a flexible coupling such that the first hand-placement structure is configured to be displaced relative to the second hand-placement structure by a predetermined amount.

42. The hand cleaning device of clause 31, wherein the device enclosure structure comprises a degradable material.

43. A unitary hand-held device comprising:
a first hand-placement structure comprising an outer surface configured to receive a palm of a first hand of a user;
a second hand-placement structure, that with respect to a first horizontal axis, opposes the first hand placement structure, and further configured to receive a palm of a second hand of the same user while the first hand is received within the first hand placement structure such that during usage of the device, the user's first palm and second palm face each other with respect to the first horizontal axis;
a channel, positioned, with respect to the horizontal axis, between the first hand-placement structure's outer surface and the second hand-placement structure's outer surface, configured to receive a plurality of digits of each of the first and the second hand of the user, wherein an outermost perimeter of each of the hand placement structures are larger than an outermost perimeter of the channel with respect to a distance along a perpendicular direction from the first horizontal axis; and
an interior outlet within the channel, for releasing a cleaning agent onto one or more digits of the user.

44. The device of clause 43, wherein both the hand-placement structures and the channel all have a consistent homogenous composition with respect to each other.

45. The hand-held device of clause 44, wherein the alignment structures are configured to be at least partially created by a force of the user's digits pressing into the channel.

46. The hand-held device of clause 45, wherein the channel comprises a porous compressible material configured such that, during use of the device, pores of the compressible material are configured to shut or otherwise be substantially blocked by the force of the user's digits and/or a rotational force of the device.

47. The hand-held device of clause 46, wherein the device is further configured such that a force of the user's digits and/or a rotational force of the device during use will cause the device to expose a cleaning agent held by the porous compressible material to be extruded onto at least a portion of the digits within the channel.

48. The hand-held device of clause 43, wherein the channel comprises a porous compressible material configured such that, during use of the device, pores of the compressible material are configured to shut or otherwise be substantially blocked by the force of the user's digits and/or a rotational force of the device, whereby cross-contamination between different digits is reduced or prevented.

49. The hand-held device of clause 44, wherein the channel is configured, such that during use, it has a depth dimension of at least an average length of a distal digit of a user's one or more fingers or one or more thumbs.

50. The hand-held device of clause 43, wherein a force of the user's digits and/or a rotational force of the device during use is configured to expose a cleaning agent held by the porous compressible material to be extruded onto at least a portion of digits within the channel.

51. The device of clause 43, wherein the channel comprises a first channel and a second channel, wherein the first channel is configured to receive a plurality of digits from the first hand and the second channel is configured to receive a plurality of digits from the second hand.

52. The device of clause 43, wherein the device is further configured to extrude a cleaning agent onto the palms of the user during use.

53. The device of clause 52, wherein the extrusion of the cleaning agent onto the palms is caused by at least one force along the direction of the first horizontal axis that results in shortening a length of the device along the first horizontal axis.

54. The device of clause 52, wherein the first horizontal axis is a first axis of rotation and wherein the extrusion of the cleaning agent onto the palms of the user is caused by at least one force along the axis of rotation.

55. The device of clause 43, wherein the device is configured to be flexible such that during use, the first hand placement structure is flexibly connected to the second hand placement structure, such that each is configured to permit the rotation of a plurality of digits of the first hand by at least 45 degrees with respect to the corresponding digits of the second hand placement structure about an axis of rotation that is co-linear with the first horizontal axis.

56. A unitary device for the atraumatic reduction of a level of an infectious agent on a hand of a user comprising:
  a first hand-placement structure and a second hand placement structure, that with respect to a first horizontal axis, opposes the first hand placement structure, the first and second hand-placement structures being substantially symmetrical about a centerline along the first horizontal axis of the device, and wherein the first hand-placement structure is configured to receive a first hand of the user and the second hand-placement structure is configured to receive a second hand of the user such that, during proper usage of the device, a first palm of the first hand faces a second palm of the second hand; and
  a divider region comprising a divider structure that separates the first hand-placement structure from the second hand-placement structure, and further separates one or more digits of the first hand or the second hand of the user, wherein an outermost perimeter of each of the hand placement structures are larger than an outermost perimeter of the divider with respect to a distance along a perpendicular direction from the first horizontal axis;
  wherein the divider region comprises a porous compressible material configured such that, during use of the device, pores of the compressible material are configured to shut or otherwise be substantially blocked by the force of the user's digits and/or a rotational force of the device, whereby cross-contamination between different digits is reduced or prevented.

57. The device of clause 56, wherein the first hand-placement structure, the second hand-placement structure, and the divider structure each comprise at least one compressible porous material.

58. The device of clause 56, wherein the device is configured to release a cleaning agent upon flexing the first hand-placement structure relative to the second hand-placement structure.

59. The device of clause 58, wherein the device is configured such that the release of the cleaning agent is configured to cause the extrusion of the cleaning agent onto the user's palms positioned on the hand placement structures and at least a plurality of digits of both hands positioned at the divider, and wherein the extrusion of cleaning agent onto the palms is caused by at least one force along the direction of the first horizontal axis that results in shortening a length of the device along the first horizontal axis.

60. The device of clause 56, wherein the divider region comprises a porous compressible material configured such that, during use of the device, pores of the compressible material are configured to shut or otherwise be substantially blocked by the force of the user's digits and/or a rotational force of the device, whereby cross-contamination between different digits is reduced or prevented.

61. The device of clause 54, further comprising: a plurality of alignment structures wherein an alignment structure, selected from the plurality of alignment structures, promotes separation of a pair of digits of the user during use of the device.

62. A unitary hand-held device comprising:
  a body composed of at least one compressible material and comprising a first hand-placement structure and a second-hand placement structure which are connected via a divider structure of a divider region, wherein the body is configurable to expand from a compressed state to an expanded state, wherein at the expanded state, the device is configured to expand into a substantially spherical shape at an ambient pressure and comprises:
  a first hand-placement structure comprising an outer surface configured to receive a palm of a first hand of a user;
  a second hand-placement structure, that with respect to a first horizontal axis, opposes the first hand placement structure, and further configured to receive a palm of a second hand of the same user while the first hand is received within the first hand placement structure such that during usage of the device, the user's first palm and second palms face each other with respect to the first horizontal axis; and
  a channel, positioned, with respect to the horizontal axis, between the first hand-placement structure's outer surface and the second hand-placement structure's outer surface, wherein an outermost perimeter of each of the hand-placement structures are larger than an outermost perimeter of the channel with respect to a distance along a perpendicular direction from the first horizontal axis, the channel being configured to receive at least a portion of a plurality of digits of each of the first and the second hand of the user and upon use of the device to reduce a level of infectious agents present on an underside of a nail plate of the plurality of digits as well as an area of hyponychium skin between a free margin of the nail plate and an onychodermal band of each of the plurality of digits.

What is claimed is:

1. A unitary hand-held device comprising:
a first hand-placement structure comprising an outer surface configured to receive a palm of a first hand of a user;
a second hand-placement structure, that with respect to a first horizontal axis, opposes the first hand placement structure, and further comprising an outer surface configured to receive a palm of a second hand of the same user while the first hand is received by the first hand placement structure such that during usage of the device, the user's first palm and second palm face each other with respect to the first horizontal axis; and
a digit cleaning region comprising a plurality of cavities positioned, with respect to the horizontal axis, between the first hand-placement structure's outer surface and the second hand-placement structure's outer surface, configured to receive a plurality of digits of each of the first and the second hand of the user, wherein at least a portion of the cavities are configured to, during use of the device, have a depth dimension of at least an average length of a distal aspect of the user's one or more fingers or one or more thumbs positioned within the respective cavity,
wherein an outermost perimeter of each of the outer surfaces of the hand-placement structures are larger than an outermost perimeter of the digit cleaning region with respect to a distance along a perpendicular direction from the first horizontal axis; and
an interior outlet within the digit cleaning region configured to release a cleaning agent into the cavities during use of the device,
wherein the device is configured such that during use, at least one of: a force of the user's digits and a rotational force of the device along an axis of rotation that is co-linear with the first horizontal axis is configured to expose the cleaning agent held within the device to be extruded onto the digits and at least one of: the force of the user's digits and the rotational force of the device is configured to result in an atraumatic cleaning of the distal aspect of the digit including an underside of a nail plate of the plurality of digits within the cavities as well as an area of hyponychium skin between a free margin of the nail plate and an onychodermal band of each of the plurality of digits.

2. The hand-held device of claim 1, wherein the digit cleaning region comprises a porous compressible material and at least one of the force of the user's digits and the rotational force of the device is configured to expose the cleaning agent held by the porous compressible material to be extruded onto the digits within the respective cavities.

3. The hand-held device of claim 2, wherein an inner perimeter of at least one cavity comprises the porous compressible material, and the device is configured such that during use, the inner perimeter compresses to conform to a shape of at least a portion of the perimeter of the distal aspect of the digit within the respective cavity to create a lip structure within the respective cavity configured to increase the surface area of hyponychium skin that is exposed to the cleaning agent between the free margin and the onychodermal band of the digit located in that respective cavity.

4. The hand-held device of claim 2, wherein an inner perimeter of at least one cavity comprises the porous compressible material, and the device is configured such that during use of the device, the inner perimeter compresses to conform to a shape of at least a portion of the perimeter of the distal aspect of the digit within the respective cavity; and the at least one cavity comprising the porous compressible material further comprises:
a lip structure composed of a material other than the porous compressible material, and is configured to increase the surface area of hyponychium skin that is exposed to the cleaning agent between the free margin and the onychodermal band of the digit located in the at least one cavity.

5. The hand-held device of claim 4, wherein the porous compressible material is a first compressible material having a first porosity and the lip structure is a second compressible material having a second porosity; and
wherein pores of the second compressible material are configured to shut or otherwise be substantially blocked by a first force whereas the pores of the first compressible material are configured to remain open or otherwise not be substantially blocked by the first force.

6. The hand-held device of claim 4, wherein the porous compressible material differs from the lip structure in a property selected from the group consisting of: rigidity, compressibility, density and combinations thereof.

7. The hand-held device of claim 2, wherein pores of the compressible material are configured to shut or otherwise be substantially blocked by at least one of the force of the user's digits and the rotational force of the device, such that to retain an increased amount of the extruded cleaning agent within the cavities during use.

8. The device of claim 2, wherein the device is further configured to extrude the cleaning agent onto the palms of the user via at least one outlet on the outer surface of the hand placement structures during use of the device.

9. The device of claim 1, wherein both the hand-placement structures and the digit cleaning region all have a consistent homogenous composition.

10. The hand-held device of claim 1, wherein the cavities are devoid of the cleaning agent prior to use of the device and wherein the rotational force of the device along the axis of rotation is caused, at least in part, by the user's digits within the respective cavities, and results in release of the cleaning agent.

11. The device of claim 1, wherein a majority of a total depth of at least one cavity is formed by a force of the user's digit acting upon the device.

12. The device of claim 1, wherein the device is configured to expand from a compressed configuration to an expanded configuration, wherein the device is configured to expand into a substantially spherical shape upon activation by unfolding, untwisting, or exposure to change in ambient pressure to be at the expanded configuration.

13. A unitary hand-held cleaning device configured to transition between a first state and a second state, comprising:
a body composed of at least one compressible material configured to retain a cleaning agent within at least a portion of the body;
wherein the body is configurable to transition from a first compressed state to an expanded second state upon being exposed to at least one of: an increase of an atmospheric pressure force above an atmospheric pressure threshold and a decrease in a compressive force below a compressive force threshold, wherein at the expanded state, comprises:

a first hand-placement structure comprising an outer surface configured to receive a palm of a first hand of a user;

a second hand-placement structure, that with respect to a first horizontal axis, opposes the first hand placement structure, and further configured to receive a palm of a second hand of the same user while the first hand is received within the first hand placement structure such that during usage of the device in the expanded second state, the user's first palm and second palm face each other with respect to the first horizontal axis; and digit cleaning region, positioned, with respect to the horizontal axis, between the first hand-placement structure's outer surface and the second hand-placement structure's outer surface, the region being configured to receive at least a portion of a plurality of digits of each of the first and the second hand of the user and upon use of the device to reduce a level of infectious agents present on the distal aspect of at least one digit, including but not limited to an underside of a nail plate of each of the plurality of digits as well as an area of hyponychium skin between a free margin of the nail plate and an onychodermal band of each of the plurality of digits.

14. The device of claim 13, wherein the device is further configured to extrude a cleaning agent onto the palms of the user via at least one outlet on the outer surface of the hand placement structures during use of the device.

15. The device of claim 14, wherein the device must be activated in addition to being exposed to at least one of: the atmospheric pressure force above an atmospheric pressure threshold and the compressive force below the compressive force threshold, wherein the activation comprises a twisting or rotational force upon a portion of the body.

16. The device of claim 15, wherein the device is configured such that a first twisting or first rotational force upon the body activates the device and a second compressive force upon the body is configured to release the cleaning agent into at least a portion of a plurality of cavities.

17. The device of claim 15, wherein the body is configured to be activated and release the cleaning agent into at least a portion of a plurality of cavities simultaneously upon receiving a single force above a force threshold.

18. The device of claim 13, wherein at least a portion of the body is degradable and is configured to decompose during use of the device at a rate coincident with an intended use time frame of the device, and wherein the device comprises at least a first material configured to degrade at a first rate and a second material configured to degrade at the second rate.

19. A unitary hand-held device comprising:

a first hand-placement structure comprising an outer surface configured to receive a palm of a first hand of a user;

a second hand-placement structure, that with respect to a first horizontal axis, opposes the first hand placement structure, and further comprising an outer surface configured to receive a palm of a second hand of the same user while the first hand is received by the first hand placement structure such that during usage of the device, the user's first palm and second palm face each other with respect to the first horizontal axis;

a digit cleaning region comprising a plurality of cavities positioned, with respect to the horizontal axis, between the first hand-placement structure's outer surface and the second hand-placement structure's outer surface, configured to receive a plurality of digits of each of the first and the second hand of the user, wherein at least a portion of the cavities are configured to, during use of the device, have a depth dimension of at least an average length of a distal aspect of the user's one or more fingers or one or more thumbs positioned within the respective cavity; and an interior outlet within the digit cleaning region configured to release a cleaning agent into the cavities during use of the device, wherein the device is configured such that during use, at least one of: a force of the user's digits and a rotational force of the device along an axis of rotation that is co-linear with the first horizontal axis is configured to expose the cleaning agent held within the device to be extruded onto the digits and at least one of: the force of the user's digits and the rotational force of the device is configured to result in an atraumatic cleaning of the distal aspect of the digit including an underside of a nail plate of the plurality of digits within the cavities as well as an area of hyponychium skin between a free margin of the nail plate and an onychodermal band of each of the plurality of digits, and wherein the cavities are devoid of the cleaning agent prior to use of the device and wherein the rotational force of the device along the axis of rotation is caused, at least in part, by the user's digits within the respective cavities, and results in release of the cleaning agent.

* * * * *